US008071508B2

(12) United States Patent
Keenan et al.

(10) Patent No.: US 8,071,508 B2
(45) Date of Patent: Dec. 6, 2011

(54) PROCESS FOR PREPARING PASTE-EXTRUDED SULFONAMIDE COMPOSITIONS

(75) Inventors: Josephe James Keenan, Townsend, DE (US); Luann Marshall Pugh, Newark, DE (US); Robert Thomas Roche, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 929 days.

(21) Appl. No.: 10/524,807

(22) PCT Filed: Sep. 9, 2003

(86) PCT No.: PCT/US03/28256
§ 371 (c)(1),
(2), (4) Date: Feb. 15, 2005

(87) PCT Pub. No.: WO2004/023876
PCT Pub. Date: Mar. 25, 2004

(65) Prior Publication Data
US 2006/0122060 A1    Jun. 8, 2006

Related U.S. Application Data

(60) Provisional application No. 60/468,706, filed on May 7, 2003, provisional application No. 60/410,197, filed on Sep. 12, 2002.

(51) Int. Cl.
*A01N 41/06* (2006.01)
(52) U.S. Cl. ........................ 504/333; 504/362
(58) Field of Classification Search .................. 504/348, 504/333, 362
See application file for complete search history.

(56) References Cited

U.S. PATENT DOCUMENTS

| | | | |
|---|---|---|---|
| 3,535,423 A | 10/1970 | Ordas | |
| 4,065,289 A | 12/1977 | Judd | |
| 4,383,113 A | 5/1983 | Levitt | |
| 4,937,386 A * | 6/1990 | Ueda et al. | 504/348 |
| 5,270,288 A * | 12/1993 | Riebel et al. | 504/214 |
| 5,474,971 A * | 12/1995 | Sandell | 504/367 |
| 5,569,639 A | 10/1996 | Beestman | |
| 5,658,855 A | 8/1997 | Nalewaja et al. | |
| 5,696,024 A | 12/1997 | Szamosi et al. | |
| 5,714,157 A | 2/1998 | Sandell et al. | |
| 6,022,552 A | 2/2000 | Brown et al. | |
| 6,093,682 A | 7/2000 | Arendt et al. | |
| 6,258,749 B1 * | 7/2001 | Nonomura | 504/121 |
| 6,270,025 B1 | 8/2001 | Geigle | |
| 2004/0023803 A1 | 2/2004 | Jager et al. | |

FOREIGN PATENT DOCUMENTS

| | | |
|---|---|---|
| JP | HEI 6-219903 | 8/1994 |
| JP | HEI 6-239711 | 8/1994 |
| JP | 8-283108 | 10/1996 |
| JP | HEI 11-12111 | 1/1999 |
| JP | 2000-72602 | 3/2000 |
| JP | P2001-233717 A | 8/2001 |
| JP | P2002-12509 A | 1/2002 |
| WO | 89/00079 | 1/1989 |
| WO | WO 93/16596 | 9/1993 |
| WO | WO 95/08265 | 3/1995 |
| WO | WO 97/20467 | 6/1997 |
| WO | WO 00/49869 | 8/2000 |
| WO | WO 02/17718 | 3/2002 |
| WO | WO 2005/120227 | 12/2005 |
| ZA | 2002/06143 | 4/2003 |

OTHER PUBLICATIONS

Johnson et al., Agricultural MU Guide, "Cleaning Field Sprayers to Avoid Crop Injury" Published by MU Extension, University of Missouri-Columbia, Nov. 1997, pp. 1-6.
Peterson et al., Kansas State Univeristy, "Cleaning Field Sprayers", Apr. 1998.
Green, J.M. 1999a. Optimizing alcohol ethoxytate surfactant activity at low doses. Weed Technol. 13:737-740.
Green, J.M. 1999b. Effect of nonylphenol ethoxytation on the biological activity of three herbicides with different water solubilities. Weed Technol. 13:840-842.
Nalewaja, J.D. and R. Matyslak. 2001. Nicosulfuron response to adjuvants, salts, and spray volume. In Hans de Ruiter, Ed. Sixth International Symposium on Adjuvant for Agrochemicals, ISAA 2001 Foundation, Amsterdam, pp. 304-314.
Russell, M.H., Saladini. J.L., and F. Lichtner. 2002. Sulfonyturea herbicides. Pesticide Outlook 13:166-173.
Streibig, J.C., Rudemo, M., and J.E. Jensen. 1993. Dose-response curves and statistical models.In J.C. Streibig and P. Kudsk, eds. Herbicide Bioassays. Boca Raton, FL: CRC Press pp. 30-55.
Woznica Z., J.D. Nalewaja, and C.G. Messersmith. 2001. Sulfosulfuron efficacy is affected by surfactants, pH of spray mixtures, and salts, Pesticide Formulations and Application Systems: A New Century for Agricultural Formulations, Twenty First Volume, ASTM STP 1414, J.C. Mueninghoff, A.K. Viets, and R.A.. Downer, Eds., American Society for Testing and Materials, West Conshohocken, PA, pp. 11-22.
Roggenbuck, F.C., Penner, D., Burrow, R.F., Thomas B. 1993. Study of the enhancement of herbicide activity and rainfastness by an organosilicone adjuvant utilizing radiolabelled herbicide and adjuvant. Pestic. Sci. 37:121-125.
Dr. Alan Rawle et al., Basic Principles of Particle Size Analysis. pp. 1-8. Malvem Instruments Ltd., Malvern, Worcestershire, UK.
Kennedy, M.W., Wilkowski, S.P., and R.C. Grimes. 1998. Formulating with trisiloxane surfactants: pH stability. p. 73-78 in Patrick McMullan, Ed. fifth International Symposium on Adjuvant for Agrochemicals vol. 1, Chemical Producers and Distributors Association, Memphis, TN.
Abstract re JP8-283108 (1997).
DuPont™ Escort® XP and Oust® XP herbicides sheet (2002).
Water Dispersible Granule Formulations May 1999—pp. 1-8 (1999).
Water Dispersible Granule Formulations Sep. 1999—pp. 1-9 (1999).
Water Dispersible Granule Formulations Jun. 2001—pp. 1-10 (2001).
Water Dispersible Granule Formulations Oct. 2001—pp. 1-12 (2001).

*Primary Examiner* — Rebecca Prouty
*Assistant Examiner* — Danielle Sullivan

(57) ABSTRACT

Paste-extruded sulfonamide herbicide compositions having improved spray equipment clean-out properties are made by preparing a mixture comprising a sulfonamide herbicide free acid, at least about 50 equivalent % of an inorganic base relative to the sulfonamide herbicide free acid and sufficient water to form an extrudable past, extruding the mixture to form an extrudate, and drying the extrudate.

39 Claims, No Drawings

PROCESS FOR PREPARING PASTE-EXTRUDED SULFONAMIDE COMPOSITIONS

This application represents a national filing under 35 U.S.C. 371 of International Application No. PCT/US2003/028256 filed Sep. 9, 2003, and claims priority of U.S. Provisional Application No. 60/468,706 filed May 7, 2003, and U.S. Provisional Application No. 60/410,197 filed Sep. 12, 2002.

BACKGROUND OF THE INVENTION

Since the discovery of the sulfonamide herbicides comprising the sulfonylureas and triazolopyrimidines, more than two dozen sulfonylurea and close to a half dozen triazolopyrimidine herbicides have been commercially developed for selective weed control in a wide variety of crops (*The Pesticide Manual, Twelfth Edition*, C. D. S. Tomlin, ed., British Crop Protection Council, Surrey, U.K, 2000). As the mode of action of these sulfonamide herbicides is inhibition of the enzyme acetolactate synthase (ALS) found in plants but not animals, sulfonamide herbicides provide a valued combination of excellent efficacy against weeds with low use rates and very low toxicity to animals.

Sulfonamide herbicides like other agricultural chemicals can be formulated as concentrates in a variety of different forms, including liquid compositions such as emulsifiable concentrates and solid compositions such as wettable powders and granules. Granular compositions can be conveniently transferred and measured like a liquid, but unlike liquids, very little residue adheres to the walls of the product container. Furthermore, organic solvents and vapors are avoided. Compared to wettable powders, granules are relatively dust-free. A particularly useful type of granules are those which are water-dispersible. Water-dispersible granules, sometimes described as "dry flowables", readily disintegrate when added to water to form a solution or suspension, which can then be sprayed on the locus to be treated. It is also advantageous for granular compositions to have good attrition resistance, low tackiness, and uniform bulk density.

Water-dispersible granules can be manufactured by a variety of processes, including fluid-bed granulation, pan granulation, spray drying, intensive mixing, compaction, paste extrusion and heat extrusion (such as melt extrusion). The physical dimensions and porosity of water-dispersible granules depends upon the manufacturing process used. Fluid bed granulation, spray drying and intensive mixing give granules that very rapidly break up and disperse in water because of granule dimensional properties such as small size, irregular surface and porosity. On the other hand, paste extrusion and heat extrusion provide granules of relatively consistent diameter and shape. The consistent diameter of extruded granules makes them useful in uniform blends as described in U.S. Pat. No. 6,022,552.

Granule composition is an important factor for obtaining sufficiently rapid dispersion of extruded granules. The dispersed particles formed on dilution should be no larger than 50 microns in their largest dimension to avoid premature settling, which may result in uneven application of the pesticide. It is therefore necessary that all of the components of the formulated product rapidly and completely disperse or dissolve in the dilution water. (If all of the components completely dissolve, then they can be regarded as being dispersed at the molecular level.) Water dispersibility of granules is determined not only by the composition of the granules but also by the composition and other properties of the aqueous medium to which the granules are added. For example, low temperatures and high concentrations of solutes can greatly retard granule disintegration.

Extruded granules are often most conveniently and cost-effectively prepared through paste extrusion using water to plasticize a powder mixture, which is then dried after extrusion. Paste extrusion avoids need for including binders that soften at elevated temperatures, as is required for heat extrusion. However, the use in paste extrusion of water as a plasticizer precludes inclusion of water-activated gas-generating ingredients, which otherwise can be used for accelerating disintegration and dispersion of heat-extruded or compacted granules.

Besides achieving satisfactory granule disintegration and dispersion, spray equipment clean-out can also be important. As sulfonamide herbicides comprise a highly active class of herbicides, it is desirable to clean out spray equipment before the equipment is subsequently used to treat a crop sensitive to the sulfonamide herbicide used in the previous application. Clean-out may require a rinsing procedure that is time-consuming and results in wastewater requiring proper environmental disposal. Furthermore, clean-out can be affected if the spray equipment contains organic deposits remaining from previous crop protection chemical applications or from other chemicals tank-mixed with the sulfonamide herbicide composition.

PCT Patent Application Publication WO 93/16596 describes a method for reducing residual sulfonylurea herbicide contamination of spray equipment by requiring as the first step the formulation of the sulfonylurea active ingredient in the form of an agriculturally suitable water soluble salt. Although a variety of methods are known for preparation of salts of sulfonamide herbicides from the corresponding free acid forms, as processes to prepare sulfonamide herbicide active ingredient often provide the free acid form either directly or as part of isolation, conversion to a salt would require an additional process step. Preferable would be formulations with improved spray equipment clean-out properties whereby the free acid form of the sulfonamide herbicide is directly used in the formulation process.

Now discovered is a process for conveniently preparing paste-extruded granular sulfonamide herbicide formulations that not only have satisfactory water dispersibility but also improved spray equipment clean-out properties.

SUMMARY OF THE INVENTION

This invention relates to a process for preparing a paste-extruded sulfonamide herbicide composition comprising
(a) preparing a mixture comprising
(i) from 2 to 90% by weight on a water-free basis of one or more active ingredients comprising at least one sulfonamide herbicide free acid;
(ii) from 0 to 95% by weight on a water-free basis of one or more additives selected from the group consisting of wetting agents, dispersants, lubricants, anticaking agents, chemical stabilizers and diluents; and
(iii) at least about 50 equivalent % of base selected from inorganic base equivalents having conjugate acid $pK_a$s at least 2.1 units greater than the highest $pK_a$ of the sulfonamide herbicide free acid component;
the sum of the weight percents of all the ingredients in the mixture totaling 100% on a water-free basis; and
(iv) sufficient water to make the mixture an extrudable paste;
(b) extruding the mixture prepared in (a) through a die or screen to form extrudate; and
(c) drying the extrudate.

The invention also relates to a paste-extruded sulfonamide herbicide composition prepared by the aforementioned process.

DETAILED DESCRIPTION OF THE INVENTION

It has been discovered that a paste-extruded sulfonamide herbicide composition having not only excellent water dispersibility but significantly improved spray equipment clean-out properties is obtained from extrusion of a mixture comprising at least one sulfonamide herbicide free acid by including in the mixture for extrusion at least about 50 equivalent % of base selected from inorganic base equivalents having conjugate acid $pK_a$s at least 2.1 units greater than the $pK_a$ of the sulfonamide herbicide free acid with the highest $pK_a$. By sulfonamide herbicide free acid is meant the free acid form of the sulfonamide herbicide and not the salt form (wherein the sulfonamide herbicide is deprotonated at its acidic sulfonamide center). The mixture for extrusion can also comprise the salt form of one or more sulfonamide herbicides among the mixture components, but only the sulfonamide herbicide acid form present is considered to calculate the at least about 50 equivalent % of base selected from inorganic base equivalents. Commonly the sulfonamide herbicides added to prepare the mixture for extrusion are at least 10% in the acid form, typically at least 50%, more typically at least 80% and most typically at least 90% in the acid form.

The $pK_a$ values of the sulfonamide herbicides are determined in water at ambient temperatures, typically about 20 to 25° C. $pK_a$ values can be determined by standard methods such as the procedure taught below in Analytical Example 1, and measured values for commercial herbicides are generally published in such references as *The Pesticide Manual, Twelfth Edition* edited by C. D. S. Tomlin (British Crop Protection Council, Surrey, UK, 2000). For the convenience of the reader, Table A below lists $pK_a$ values for many of the commercially available sulfonamide herbicides.

TABLE A

Molecular Weights and $pK_a$ Values of Some Sulfonamide Herbicides

| Sulfonamide | Mol. Wt. | $pK_a$ |
|---|---|---|
| Sulfonylureas | | |
| amidosulfuron | 369.4 | 3.6 |
| azimsulfuron | 424.4 | 3.6 |
| bensulfuron-methyl | 410.4 | 5.2 |
| chlorimuron-ethyl | 414.8 | 4.2 |
| chlorsulfuron | 357.8 | 3.6 |
| cinosulfuron | 413.4 | 4.7 |
| cyclosulfamuron | 421.4 | 5.0 |
| ethametsulfuron-methyl | 410.4 | 4.6 |
| flazasulfuron | 407.3 | 4.4 |
| flupyrsulfuron-methyl | 465.4 | 4.9 |
| halosulfuron-methyl | 434.8 | 3.4 |
| imazosulfuron | 412.8 | 4.0 |
| iodosulfuron-methyl | 507.3 | 3.2 |
| metsulfuron-methyl | 381.4 | 3.3 |
| nicosulfuron | 410.4 | 4.6 |
| oxasulfuron | 406.4 | 5.1 |
| primisulfuron-methyl | 468.3 | 3.5 |
| prosulfuron | 419.4 | 3.8 |
| pyrazosulfuron-ethyl | 414.4 | 3.7 |
| rimsulfuron | 431.4 | 4.0 |
| sulfometuron-methyl | 364.4 | 5.2 |
| sulfosulfuron | 470.5 | 3.5 |
| thifensulfuron-methyl | 387.4 | 4.0 |
| triasulfuron | 401.8 | 4.6 |
| tribenuron-methyl | 395.4 | 5.0 |

TABLE A-continued

Molecular Weights and $pK_a$ Values of Some Sulfonamide Herbicides

| Sulfonamide | Mol. Wt. | $pK_a$ |
|---|---|---|
| trifloxysulfuron | 437.1 | 4.8 |
| triflusulfuron-methyl | 492.4 | 4.4 |
| Triazolopyrimidines | | |
| florasulam | 359.3 | 4.5 |
| metosulam | 418.3 | 4.8 |
| flumetsulam | 325.3 | 4.6 |
| diclosulam | 406.2 | 4.0 |
| cloransulam-methyl | 429.8 | 4.8 |
| penoxsulam | 483.4 | 5.1 |

The at least about 50 equivalent % of base in the mixture for extrusion according to this invention is selected from base equivalents that are inorganic, i.e. provided by inorganic bases. Particularly suitable inorganic bases are described in further detail below. The terms "equivalent % of base" and "base equivalents" refers to the fact that some inorganic bases can provide more than one equivalent of basicity per mole. In the context of the present invention, the number of base equivalents per mole of base is limited to the base equivalents having conjugate acid $pK_a$s at least 2.1 units greater that the highest $pK_a$ of the one or more sulfonamide free acid components in the mixture. Calculation of number of moles of base needed to provide at least 50 equivalent % of base is described further below.

The $pK_a$ values of conjugate acids of bases can be determined by standard methods. Published values can be found in a variety of references, such as *The Chemist's Companion* by A. J. Gordon and R. A. Ford (Wiley-Interscience, New York, 1972). For the convenience of the reader, Table B lists conjugate acid $pK_a$ values for some common bases.

TABLE B

Formula Weights and Conjugate Acid $pK_a$ Values of Some Bases

| Base | Form. Wt. | First $pK_a$ | Second $pK_a$ | Third $pK_a$ |
|---|---|---|---|---|
| LiOH | 23.95 | 14.0 | — | — |
| $Li_2CO_3$ | 73.89 | 10.2 | 6.4 | — |
| $Li_3PO_4$ | 115.79 | 12.7 | 7.2 | 2.1 |
| NaOH | 40.00 | 14.0 | — | — |
| $NaHCO_3$ | 84.01 | 6.4 | — | — |
| $Na_2CO_3$ | 105.99 | 10.2 | 6.4 | — |
| $Na_2CO_3.H_2O$ | 124.01 | 10.2 | 6.4 | — |
| $Na_2HPO_4$ | 141.96 | 7.2 | 2.1 | — |
| $Na_3PO_4$ | 163.94 | 12.7 | 7.2 | 2.1 |
| $Na_3PO_4.12H_2O$ | 380.13 | 12.7 | 7.2 | 2.1 |
| $Na_4P_2O_7$ | 265.90 | 9.0 | 7.0 | 2.0 |
| KOH | 56.11 | 14.0 | — | — |
| $KHCO_3$ | 100.12 | 6.4 | — | — |
| $K_2CO_3$ | 138.21 | 10.2 | 6.4 | — |
| $K_2HPO_4$ | 174.18 | 7.2 | 2.1 | — |
| $K_3PO_4$ | 212.28 | 12.7 | 7.2 | 2.1 |
| $K_4P_2O_7$ | 330.35 | 9.0 | 7.0 | 2.0 |

The equivalent % of base selected from inorganic base equivalents is calculated relative to the total number of moles of the one or more sulfonamide herbicides added to the mixture in their free acid forms (i.e. not salts), with consideration of the basicity of the inorganic base equivalents for which conjugate acid $pK_a$ in water is a least 2.1 units greater Man the $pK_a$ of the sulfonamide herbicide with highest $pK_a$. For example, if one mole of thifensulfuron-methyl and one mole of tribenuron-methyl in their free acid forms is added to the mixture, the $pK_a$ of tribenuron-methyl (5.0) is considered instead of the $pK_a$ of thifensulfuron-methyl (4.0), as the former $pK_a$ is higher. In this example, the total number of moles of sulfonamide herbicides in free acid form is two moles, and 50 equivalent % of an inorganic base would require one equivalent of base. Phosphoric acid contains three acidic hydrogen atoms, with respective aqueous $pK_a$ of 2.1, 7.2 and 12.7. As only 7.2 and 12.7 are least 2.1 units greater than 5.0, sodium phosphate is dibasic (i.e. provides two base equivalents per mole) relative to the requirement that $pK_a$ difference be at least 2.1 units. Accordingly one equivalent of base would be provided by one-half mole (i.e. one-half formula weight amount) of sodium phosphate. Carbonic acid contains two acidic hydrogen atoms, with respective aqueous $pK_a$ of 6.4 and 10.2. As only 10.2 is at least 2.1 units greater than 5.0, sodium carbonate is monobasic (i.e. provides one base equivalent per mole) relative to the requirement that the $pK_a$ difference be at least 2.1 units. Therefore one mole (i.e. one formula weight amount) of sodium carbonate would provide one equivalent of base.

With many sulfonamide herbicides, particularly those with a solubility in pH 7 buffered water at ambient temperature (i.e. about 20 to 30° C.) of greater than about 1000 mg/L, compositions prepared according to the process of this invention to include about 50 equivalent % of base relative to the sulfonamide herbicide free acids will substantially reduce residues in spray equipment. The addition of base is particularly beneficial for paste-extruded compositions of sulfonamide herbicides with a solubility in pH 7 buffered water of less than about 10,000 mg/L, because for more soluble sulfonamide herbicides spray tank residues are rarely encountered. (Illustrative examples of sulfonamide herbicides having a solubility in pH 7 buffered water between 1000 and 10,000 mg/L are chlorimuron-ethyl, metsulfuron-methyl, thifensulfuron-methyl and tribenuron-methyl.) With sulfonamide herbicides having a solubility in pH 7 buffered water of less than about 1000 mg/L, more than 50 equivalent % of base relative to the sulfonamide herbicide free acids may be needed in the compositions prepared according to the process of this invention to significantly reduce residues in spray equipment. (Illustrative examples of sulfonamide herbicides having a solubility in pH 7 buffered water less than 1000 mg/L are bensulfuron-methyl and sulfometuron-methyl.) For compositions of these sulfonamide herbicides, typically about 75 to 100 equivalent % of base significantly reduces spray residues, and greater amounts (i.e. up to about 200 equivalent %) of base may be useful in reducing residues to negligible levels. Solubility of sulfonamide herbicides in pH 7 buffered water can be determined by standard methods such as the procedure taught below in Analytical Example 2.

Therefore to improve spray equipment clean-out properties, the mixture for extrusion according to the process of this invention preferably contains at least about 75 equivalent % of base, and more preferably at least about 100 equivalent % of base relative to the one or more sulfonamide herbicide free acids. Furthermore, if the mixture contains acidic substances besides the sulfonamide herbicide free acids, correspondingly more base should be added. More than 100 equivalent % of base can be included relative to the one or more sulfonamide herbicide free acids, provided that the mixture does not include ingredients unstable to the base.

The base in the mixture for extrusion according to the process of this invention comprises at least one inorganic base. Inorganic bases particularly suitable for this invention include those having cations derived from alkali metals or ammonium, and counterions selected from carbonate, phosphate, oxide, hydroxide and silicate anions, including dimeric, trimeric and polymeric forms such as pyrophosphate, tripolyphosphate, polyphosphate, trisilicate, etc. Illustrative inorganic bases include but are not limited to sodium phosphate ($Na_3PO_4$), sodium hydrogen phosphate ($Na_2HPO_4$), potassium phosphate ($K_3PO_4$), potassium hydrogen phosphate ($K_2HPO_4$), ammonium hydrogen phosphate (($NH_4)_2HPO_4$), sodium carbonate ($Na_2CO_3$), sodium hydrogen carbonate ($NaHCO_3$), potassium carbonate ($K_2CO_3$), potassium hydrogen carbonate ($KHCO_3$), lithium oxide ($Li_2O$), lithium hydroxide (LiOH), lithum carbonate ($Li_2CO_3$), sodium hydroxide (NaOH), lithium phosphate ($Li_3PO_4$), lithium metasilicate ($Li_2SiO_3$), lithium orthosilicate ($Li_4SiO_4$), potassium hydroxide (KOH), sodium metasilicate ($Na_2SiO_3$), sodium orthosilicate ($Na_4SiO_4$), potassium pyrophosphate ($K_4P_2O_7$), sodium trimetaphosphate (($NaPO_3)_3$), sodium hexametaphosphate (($NaPO_3)_6$), sodium polyphosphate (($NaPO_3)_n$), sodium pyrophosphate ($Na_4P_2O_7$), sodium tripolyphosphate (sodium triphosphate, $Na_5P_3O_{10}$) and sodium trisilicate ($Na_2Si_3O_7$), including their anhydrous and hydrated forms.

Preferred for reason of cost, effectiveness and convenience are inorganic bases containing an alkali metal cation selected from sodium ($Na^+$) and potassium ($K^+$), more preferably sodium. Also preferred for reason of cost, effectiveness and convenience are inorganic bases containing a counterion selected from hydrogen carbonate ($HCO_3^-$), carbonate ($CO_3^{2-}$), hydrogen phosphate ($HPO_4^{2-}$) and phosphate ($PO_4^{3-}$), more preferably carbonate and phosphate. Preferred inorganic bases thus include sodium hydrogen carbonate, sodium carbonate, sodium hydrogen phosphate, sodium phosphate, potassium hydrogen carbonate, potassium carbonate, potassium hydrogen phosphate and potassium phosphate. These inorganic bases include hydrated forms such as sodium carbonate monohydrate, sodium hydrogen phosphate heptahydrate, sodium phosphate dodecahydrate, potassium carbonate sesquihydrate, potassium hydrogen phosphate trihydrate and potassium phosphate octahydrate. Inorganic bases more preferred are sodium carbonate, sodium phosphate, potassium carbonate and potassium phosphate, including hydrated forms thereof. A most preferred inorganic base is sodium carbonate, including hydrated forms thereof. Another most preferred inorganic base is sodium phosphate, including hydrated forms thereof. While inorganic bases are useful alone, mixtures of inorganic bases may be advantageous.

During the addition of water to prepare an extrudable paste, the heat of hydration of anhydrous bases can, depending upon amount and nature of base and the cooling capacity of the mixing or kneading equipment, cause considerable increase in temperature with potentially undesirable effect on the chemical constitution and/or extrudability of the paste. If the temperature increase caused by anhydrous bases would be excessive, hydrated instead of anhydrous forms of bases are preferred for preparing the mixture for extrusion. As the heat of hydration of anhydrous sodium phosphate is particularly large, the dodecahydrate is a preferred form of sodium phosphate for the process of this invention.

Sulfonamide herbicides have as an essential molecular structure feature a sulfonamide moiety (—S(O)$_2$NH—). As referred to herein, sulfonamide herbicides particularly comprise sulfonylurea herbicides wherein the sulfonamide moiety is a component in a sulfonylurea moiety (—S(O)$_2$NHC(O)NH(R)—) and triazolopyrimidine herbicides wherein the sulfonyl end of the sulfonamide moiety is connected to the 2-position of a substituted [1,2,4]triazolopyrimidine ring system and the amino end of the sulfonamide moiety is connected to a substituted aryl, typically phenyl, group. In sulfonylurea herbicides the sulfonyl end of the sulfonylurea moiety is connected either directly or by way of an oxygen atom or an optionally substituted amino or methylene group to a typically substituted cyclic or acyclic group. At the opposite end of the sulfonylurea bridge, the amino group, which may have a substituent such as methyl (R being CH$_3$) instead of hydrogen, is connected to a heterocyclic group, typically a symmetric pyrimidine or triazine ring, having one or two substituents such as methyl, ethyl, trifluoromethyl, methoxy, ethoxy, methylamino, dimethylamino, ethylamino and the halogens.

Representative of the sulfonylureas contemplated for use in this invention are those of the formula:

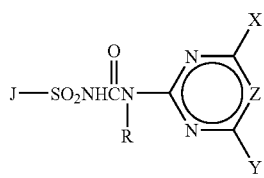

wherein:

J is selected from the group consisting of

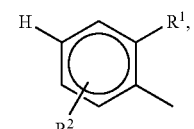
J-1

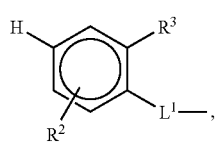
J-2

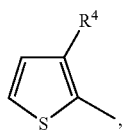
J-3

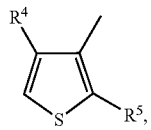
J-4

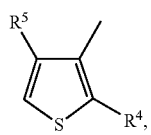
J-5

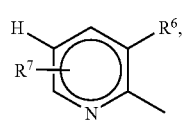
J-6

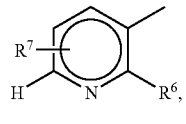
J-7

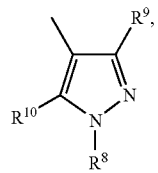
J-8

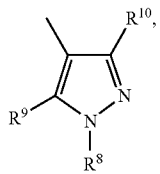
J-9

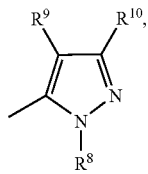
J-10

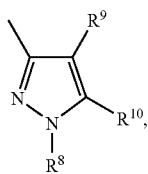
J-11

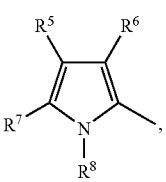
J-12

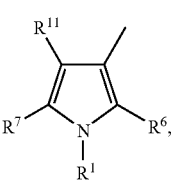
J-13

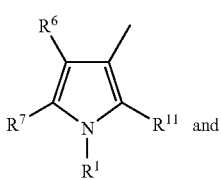
J-14

J-15

J is R$^{13}$SO$_2$N(CH$_3$)—;

R is H or CH$_3$;

R$^1$ is F, Cl, Br, NO$_2$, C$_1$-C$_4$ alkyl, C$_1$-C$_4$ haloalkyl, C$_3$-C$_4$ cycloalkyl, C$_2$-C$_4$ haloalkenyl, C$_1$-C$_4$ alkoxy, C$_1$-C$_4$ haloalkoxy, C$_2$-C$_4$ alkoxyalkoxy, CO$_2$R$^{14}$, C(O)NR$^{15}$R$^{16}$, SO$_2$NR$^{17}$R$^{18}$, S(O)$_n$R$^{19}$, C(O)R$^{20}$, CH$_2$CN or L;

R$^2$ is H, F, Cl, Br, I, CN, CH$_3$, OCH$_3$, SCH$_3$, CF$_3$ or OCF$_2$H;

$R^3$ is Cl, $NO_2$, $CO_2CH_3$, $CO_2CH_2CH_3$, $C(O)CH_3$, $C(O)CH_2CH_3$, $C(O)$-cyclopropyl, $SO_2N(CH_3)_2$, $SO_2CH_3$, $SO_2CH_2CH_3$, $OCH_3$ or $OCH_2CH_3$;

$R^4$ is $C_1$-$C_3$ alkyl, $C_1$-$C_2$ haloalkyl $C_1$-$C_2$ alkoxy, $C_2$-$C_4$ haloalkenyl, F, Cl, Br, $NO_2$, $CO_2R^{14}$, $C(O)NR^{15}R^{16}$, $SO_2NR^{17}R^{18}$, $S(O)_nR^{19}$, $C(O)R^{20}$ or L;

$R^5$ is H, F, Cl, Br or $CH_3$;

$R^6$ is $C_1$-$C_3$ alkyl, $C_1$-$C_2$ alkoxy, $C_2$-$C_4$ haloalkenyl, F, Cl, Br, $CO_2R^{14}$, $C(O)NR^{15}R^{16}$, $SO_2NR^{17}R^{18}$, $S(O)_nR^{19}$, $C(O)R^{20}$ or L;

$R^7$ is H, F, Cl, $CH_3$ or $CF_3$;

$R^8$ is H, $C_1$-$C_3$ alkyl or pyridyl;

$R^9$ is $C_1$-$C_3$ alkyl, $C_1$-$C_2$ alkoxy, F, Cl, Br, $NO_2$, $CO_2R^{14}$, $SO_2NR^{17}R^{18}$, $S(O)_nR^{19}$, $OCF_2H$, $C(O)R^{20}$, $C_2$-$C_4$ haloalkenyl or L;

$R^{10}$ is H, Cl, F, Br, $C_1$-$C_3$ alkyl or $C_1$-$C_2$ alkoxy, $R^{11}$ is H, $C_1$-$C_3$ alkyl, $C_1$-$C_2$ alkoxy, $C_2$-$C_4$ haloalkenyl, F, Cl, Br, $CO_2R^{14}$, $C(O)NR^{15}R^{16}$, $SO_2NR^{17}R^{18}$, $S(O)_nR^{19}$, $C(O)R^{20}$ or L;

$R^{12}$ is halogen, $C_1$-$C_4$ alkyl or $C_1$-$C_3$ alkylsulfonyl;

$R^{13}$ is $C_1$-$C_4$ alkyl;

$R^{14}$ is selected from the group consisting of allyl, propargyl, oxetan-3-yl and $C_1$-$C_3$ alkyl optionally substituted by at least one member independently selected from halogen, $C_1$-$C_2$ alkoxy and CN;

$R^{15}$ is H, $C_1$-$C_3$ alkyl or $C_1$-$C_2$ alkoxy, $R^{16}$ is $C_1$-$C_2$ alkyl;

$R^{17}$ is H, $C_1$-$C_3$ alkyl, $C_1$-$C_2$ alkoxy, allyl or cyclopropyl;

$R^{18}$ is H or $C_1$-$C_3$ alkyl;

$R^{19}$ is $C_1$-$C_3$ alkyl, $C_1$-$C_3$ haloalkyl, allyl or propargyl;

$R^{20}$ is $C_1$-$C_4$ alkyl, $C_1$-$C_4$ haloalkyl or $C_3$-$C_5$ cycloalkyl optionally substituted by halogen;

n is 0, 1 or 2;

L is

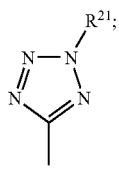

$L^1$ is $CH_2$, NH or O;

$R^{21}$ is selected from the group H and $C_1$-$C_3$ alkyl;

X is selected from the group H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino and di($C_1$-$C_3$ alkyl)amino;

Y is selected from the group H, $C_1$-$C_4$ alkyl, $C_1$-$C_4$ alkoxy, $C_1$-$C_4$ haloalkoxy, $C_1$-$C_4$ alkylthio, $C_1$-$C_4$ haloalkylthio, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_2$-$C_5$ alkylsulfinylalkyl, $C_2$-$C_5$ alkylsulfonylalkyl, $C_1$-$C_4$ haloalkyl, $C_2$-$C_4$ alkynyl, $C_3$-$C_5$ cycloalkyl, azido and cyano; and Z is selected from the group CH and N;

provided that (i) when one or both of X and Y is $C_1$ haloalkoxy, then Z is CH; and (ii) when X is halogen, then Z is CH and Y is $OCH_3$, $OCH_2CH_3$, $N(OCH_3)CH_3$, $NHCH_3$, $N(CH_3)_2$ or $OCF_2H$.

Representative of the triazolopyrimidines contemplated for use in this invention are those of the formula:

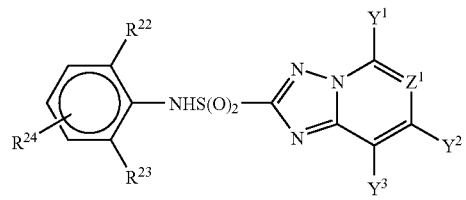

wherein:

$R^{22}$ and $R^{23}$ are each independently selected from halogen, nitro, $C_1$-$C_4$ alkyl, $C_1$-$C_4$ haloalkyl, $C_1$-$C_4$ alkoxy, $C_1$-$C_4$ haloalkoxy and $C_2$-$C_3$ alkoxycarbonyl;

$R^{24}$ is selected from H, halogen, $C_1$-$C_4$ alkyl and $C_1$-$C_2$ alkoxy, $Y^1$ is selected from H, $C_1$-$C_2$ alkyl and $C_1$-$C_2$ alkoxy, $Y^2$ is selected from H, F, Cl, Br, $C_1$-$C_2$ alkyl and $C_1$-$C_2$ alkoxy, $Y^3$ is selected from H, F and methoxy, and $Z^1$ is selected from CH and N;

provided that at least one of $Y^1$ and $Y^2$ is other than H.

Of note are said triazolopyrimidines wherein $Y^3$ is H or F.

In the above recitations, the term "alkyl", used either alone or in compound words such as "alkylthio" or "haloalkyl" includes straight-chain or branched alkyl, such as, methyl, ethyl, n-propyl, i-propyl, or the different butyl isomers. "Cycloalkyl" includes, for example, cyclopropyl, cyclobutyl and cyclopentyl. "Alkenyl" includes straight-chain or branched alkenes such as ethenyl, 1-propenyl, 2-propenyl, and the different butenyl isomers. "Alkenyl" also includes polyenes such as 1,2-propadienyl and 2,4-butadienyl. "Alkynyl" includes straight-chain or branched alkynes such as ethynyl, 1-propynyl, 2-propynyl and the different butynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkenyloxy" includes straight-chain or branched alkenyloxy moieties. Examples of "alkenyloxy" include $H_2C=CHCH_2O$, $(CH_3)CH=CHCH_2O$ and $CH_2=CHCH_2CH_2O$. "Alkynyloxy" includes straight-chain or branched alkynyloxy moieties. Examples of "alkynyloxy" include $HC\equiv CCH_2O$ and $CH_3C\equiv CCH_2O$. "Alkylthio" includes branched or straight-chain alkylthio moieties such as methylthio, ethylthio, and the different propylthio isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$; "alkylsulfinylalkyl" and "alkylsulfonylalkyl" include the corresponding sulfoxides and sulfones, respectively. Other substituents such as "alkylamino", "dialkylamino" are defined analogously.

The total number of carbon atoms in a substituent group is indicated by the "$C_i$-$C_j$" prefix where i and j are numbers from 1 to 5. For example, $C_1$-$C_4$ alkyl designates methyl through butyl, including the various isomers. As further examples, $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkoxy", "haloalkylthio", and the like, are defined analogously to the term "haloalkyl". Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$.

The following sulfonylurea herbicides illustrate the sulfonylureas useful for this invention: amidosulfuron (N-[[[[(4,6-dimethoxy-2-pyrimdinyl)amino]carbonyl]amino]-sulfonyl]-N-methylmethanesulfonamide), azimsulfuron (N-[[(4,6-dimethoxy-2-pyrimidinyl)-amino]carbonyl]-1-methyl-4-(2-methyl-2H-tetrazol-5-yl)-1H-pyrazole-5-sulfonamide), bensulfuron-methyl (methyl 2-[[[[[(4,6-dimethoxy-2-pyrimidinyl)amino]carbonyl]amino]-sulfonyl]methyl]benzoate), chlorimuron-ethyl (ethyl 2-[[[[(4-chloro-6-methoxy-2-pyrimdinyl)amino]carbonyl]amino]sulfonyl]benzoate), chlorsulfuron (2-chloro-N-[[(4-methoxy-6-methyl-1,3,5-triazin-2-yl)amino]carbonyl]benzenesulfonamide), cinosulfuron (N-[[[(4,6-dimethoxy-1,3,5-triazin-2-yl)amino]carbonyl]-2-(2-methoxyethoxy)benzenesulfonamide), cyclosulfamuron (N-[[[2-(cyclopropylcarbonyl)phenyl]amino]sulfonyl]-$N^1$-(4,6-dimethoxypyrimidin-2-yl)urea), ethametsulfuron-methyl (methyl 2-[[[[4-ethoxy-6-(methylamino)-1,3,5-triazin-2-yl]amino]carbonyl]amino]sulfonyl]benzoate), ethoxysulfuron (2-ethoxyphenyl [[(4,6-dimethoxy-2-pyrimidinyl)amino]carbonyl]sulfamate), flupyrsulfuron-methyl (methyl 2-[[[[(4,6-dimethoxy-2-pyrimidinyl)amino]carbonyl]-amino]sulfonyl]-6-(trifluoromethyl)-3-pyridinecarboxylate), flazasulfuron (N-[[(4,6-dimethoxy-2-pyrimidinyl)amino]carbonyl]-3-(trifluoromethyl)-2-pyridinesulfonamide), foramsulfuron (2-[[[[(4,6-dimethoxy-2-pyrimidinyl)amino]carbonyl]amino]sulfonyl](formylamino)-N,N-dimethylbenzamide), halosulfuron-methyl (methyl 3-chloro-5-[[[[(4,6-dimethoxy-2-pyrimidinyl)amino]carbonyl]amino]sulfonyl]-1-methyl-1H-pyrazole-4-carboxylate), imazosulfuron (2-chloro-N-[[(4,6-dimethoxy-2-pyrimidinyl)amino]carbonyl]-imidazo[1,2-a]pyridine-3-sulfonamide), iodosulfuron-methyl (methyl 4-iodo-2-[[[[(4-methoxy-6-methyl 1,3,5-triazin-2-yl)amino]carbonyl]amino]sulfonyl]benzoate), mesosulfuron-methyl (methyl 2-[[[[(4,6-dimethoxy-2-pyrimidinyl)amino]carbonyl]amino]sulfonyl]-4-[[(methylsulfonyl)amino]methyl]benzoate), metsulfuron-methyl (methyl 2-[[[[(4-methoxy-6-methyl-1,3,5-triazin-2-yl)amino]carbonyl]amino]sulfonyl]-benzoate), nicosulfuron (2-[[[[(4,6-dimethoxy-2-pyrimidinyl)amino]carbonyl]amino]-sulfonyl]-N,N-dimethyl-3-pyridinecarboxamide), oxasulfuron (3-oxetanyl 2-[[[[(4,6-dimethyl-2-pyrimidinyl)amino]carbonyl]amino]sulfonyl]benzoate), primisulfuron-methyl (methyl 2-[[[[[4,6-bis(trifluoromethoxy)-2-pyrimidinyl]amino]carbonyl]amino]sulfonyl]-benzoate), prosulfuron (N-[[(4-methoxy-6-methyl-1,3,5-triazin-2-yl)amino]carbonyl]-2-(3,3,3-trifluoropropyl)benzenesulfonamide), pyrazosulfuron-ethyl (ethyl 5-[[[[(4,6-dimethoxy-2-pyrimidinyl)amino]carbonyl]amino]sulfonyl]-1-methyl-1H-pyrazole-4-carboxylate), rimsulfuron (N-[[(4,6-dimethoxy-2-pyrimidinyl)amino]carbonyl]-3-(ethylsulfonyl)-2-pyridinesulfonamide), sulfometuron-methyl (methyl 2-[[[[(4,6-dimethyl-2-pyrimidinyl)amino]carbonyl]amino]sulfonyl]benzoate), sulfosulfuron (N-[[(4,6-dimethoxy-2-pyrimidinyl)amino]carbonyl]-2-(ethylsulfonyl)imidazo[1,2-a]pyridine-3-sulfonamide), thifensulfuron-methyl (methyl 3-[[[[(4-methoxy-6-methyl-1,3,5-triazin-2-yl)amino]-carbonyl]amino]sulfonyl]-2-thiophenecarboxylate), triasulfuron (2-(2-chloroethoxy)-N-[[(4-methoxy-6-methyl-1,3,5-triazin-2-yl)amino]carbonyl]benzenesulfonamide), tribenuron-methyl (methyl 2-[[[[N-(4-methoxy-6-methyl-1,3,5-triazin-2-yl)-N-methylamino]carbonyl]-amino]sulfonyl]benzoate), trifloxysulfuron (N-[[[(4,6-dimethoxy-2-pyrimidinyl)amino]-carbonyl]-3-(2,2,2-trifluoroethoxy)-2-pyridinesulfonamide), triflusulfuron-methyl (methyl 2-[[[[[4-dimethylamino)-6-(2,2,2-trifluoroethoxy)-1,3,5-triazin-2-yl]amino]carbonyl]amino]-sulfonyl]-3-methylbenzoate) and tritosulfuron (N-[[[4-methoxy-6-(trifluoromethyl)-1,3,5-triazin-2-yl]amino]carbonyl]-2-(trifluoromethyl)benzenesulfonamide).

The following sulfonylureas are preferred for use in the disclosed invention: azinmsulfuron, bensulfuron-methyl, chlorimuron-ethyl, chlorsulfuron, ethametsulfuron-methyl, flupyrsulfuron-methyl, metsulfuron-methyl, nicosulfuron, rimsulfuron, sulfometuron-methyl, thifensulfuron-methyl, tribenuron-methyl and triflusulfuron-methyl.

The following triazolopyrimidine herbicides illustrate the triazolopyrimidines useful for this invention: cloransulam-methyl (methyl 3-chloro-2-[[(5-ethoxy-7-fluoro[1,2,4]-triazolo[1,5-c]pyrimidin-2-yl)sulfonyl]amino]benzoate, diclosulam (N-(2,6-dichlorophenyl)-5-ethoxy-7-fluoro[1,2,4] triazolo[1,5-c]pyrimidine-2-sulfonamide, florasulam (N-(2,6-difluorophenyl)-8-fluoro-5-methoxy[1,2,4]triazolo[1,5-c]pyrimidine-2-sulfonamide), flumetsulam (N-(2,6-difluorophenyl)-5-methyl[1,2,4]triazolo[1,5-c]pyrimidine-2-sulfonamide), metosulam (N-(2,6-dichloro-3-methylphenyl)-5,7-dimethoxy[1,2,4]triazolo-[1,5-a]pyrimidine-2-sulfonamide) and penoxsulam (2-(2,2-difluoroethoxy)-N-(5,8-dimethoxy[1,2,4]triazolo[1,5-c]pyrimidin-2-yl)-6-(trifluoromethyl)benzenesulfonamide).

Of note for the process of this invention are sulfonamide herbicides selected from the group consisting of amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flupyrsulfuron-methyl, flazasulfuron, foramsulfuron, halosulfuron-methyl, imazosulfuron, iodosulfuron-methyl, mesosulfuron-methyl, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, trifloxysulfuron, triflusulfuron-methyl, tritosulfuron, cloransulam-methyl, diclosulam, florasulam, flumetsulam and metosulam.

Preferred embodiments include:

Preferred 1. The process of the invention wherein the mixture comprises amidosulfuron.

Preferred 1A. The process of Preferred 1 wherein the mixture comprises at least about 75 equivalent % of inorganic base relative to amidosulfuron.

Preferred 1B. The process of Preferred 1 wherein the mixture comprises at least about 100 equivalent % of inorganic base relative to amidosulfuron.

Preferred 1C. The process of Preferred 1, 1A or 1B wherein the inorganic base comprises at least one base selected from sodium carbonate, sodium hydrogen carbonate, sodium phosphate, sodium hydrogen phosphate, potassium carbonate, potassium hydrogen carbonate, potassium phosphate and potassium hydrogen phosphate, including the hydrated forms thereof.

Preferred 2. The process of the invention wherein the mixture comprises azimsulfuron.

Preferred 2A. The process of Preferred 2 wherein the mixture comprises at least about 75 equivalent % of inorganic base relative to azimsulfuron.

Preferred 2B. The process of Preferred 2 wherein the mixture comprises at least about 100 equivalent % of inorganic base relative to azimsulfuron.

Preferred 2C. The process of Preferred 2, 2A or 2B wherein the inorganic base comprises at least one base selected from sodium carbonate, sodium hydrogen carbonate, sodium phosphate, sodium hydrogen phosphate, potassium carbonate, potassium hydrogen carbonate, potassium phosphate and potassium hydrogen phosphate, including the hydrated forms thereof.

Preferred 3. The process of the invention wherein the mixture comprises bensulfuron-methyl.

Preferred 3A. The process of Preferred 3 wherein the mixture comprises at least about 100 equivalent % of inorganic base relative to bensulfuron-methyl.

Preferred 3B. The process of Preferred 3 or 3A wherein the inorganic base comprises at least one base selected from sodium carbonate, sodium phosphate, potassium carbonate and potassium phosphate, including the hydrated forms thereof.

Preferred 4. The process of the invention wherein the mixture comprises chlorimuron-ethyl Preferred 4A. The process of Preferred 4 wherein the mixture comprises at least about 75 equivalent % of inorganic base relative to chlorimuron-ethyl.

Preferred 4B. The process of Preferred 4 or 4A wherein the inorganic base comprises at least one base selected from sodium carbonate, sodium hydrogen carbonate, sodium phosphate, sodium hydrogen phosphate, potassium carbonate, potassium hydrogen carbonate, potassium phosphate and potassium hydrogen phosphate, including the hydrated forms thereof.

Preferred 5. The process of the invention wherein the mixture comprises chlorsulfuron.

Preferred 5A. The process of Preferred 5 wherein the mixture comprises at least about 75 equivalent % of inorganic base relative to chlorsulfuron.

Preferred 5B. The process of Preferred 5 wherein the mixture comprises at least about 100 equivalent % of inorganic base relative to chlorsulfuron.

Preferred 5C. The process of Preferred 5, 5A or 5B wherein the inorganic base comprises at least one base selected from sodium carbonate, sodium hydrogen carbonate, sodium phosphate, sodium hydrogen phosphate, potassium carbonate, potassium hydrogen carbonate, potassium phosphate and potassium hydrogen phosphate, including the hydrated forms thereof.

Preferred 6. The process of the invention wherein the mixture comprises cinosulfuron.

Preferred 6A. The process of Preferred 6 wherein the mixture comprises at least about 75 equivalent % of inorganic base relative to cinosulfuron.

Preferred 6B. The process of Preferred 6 wherein the mixture comprises at least about 100 equivalent % of inorganic base relative to cinosulfuron.

Preferred 6C. The process of Preferred 6, 6A or 6B wherein the inorganic base comprises at least one base selected from sodium carbonate, sodium phosphate, sodium hydrogen phosphate, potassium carbonate, potassium phosphate and potassium hydrogen phosphate, including the hydrated forms thereof.

Preferred 7. The process of the invention wherein the mixture comprises cyclosulfamuron.

Preferred 7A. The process of Preferred 7 wherein the mixture comprises at least about 75 equivalent % of inorganic base relative to cyclosulfamuron.

Preferred 7B. The process of Preferred 7 wherein the mixture comprises at least about 100 equivalent % of inorganic base relative to cyclosulfamuron.

Preferred 7C. The process of Preferred 7, 7A or 7B wherein the inorganic base comprises at least one base selected from sodium carbonate, sodium phosphate, sodium hydrogen phosphate, potassium carbonate, potassium phosphate and potassium hydrogen phosphate, including the hydrated forms thereof.

Preferred 8. The process of the invention wherein the mixture comprises ethametsulfuron-methyl.

Preferred 8A. The process of Preferred 8 wherein the mixture comprises at least about 75 equivalent % of inorganic base relative to ethametsulfuron-methyl.

Preferred 8B. The process of Preferred 8 wherein the mixture comprises at least about 100 equivalent % of inorganic base relative to ethametsulfuron-methyl.

Preferred 8C. The process of Preferred 8, 8A or 8B wherein the inorganic base comprises at least one base selected from sodium carbonate, sodium phosphate, sodium hydrogen phosphate, potassium carbonate, potassium phosphate and potassium hydrogen phosphate, including the hydrated forms thereof.

Preferred 9. The process of the invention wherein the mixture comprises ethoxysulfuron.

Preferred 9A. The process of Preferred 9 wherein the mixture comprises at least about 75 equivalent % of inorganic base relative to ethoxysulfuron.

Preferred 9B. The process of Preferred 9 wherein the mixture comprises at least about 100 equivalent % of inorganic base relative to ethoxysulfuron.

Preferred 9C. The process of Preferred 9, 9A or 9B wherein the inorganic base comprises at least one base selected from sodium carbonate, sodium phosphate, sodium hydrogen phosphate, potassium carbonate, potassium phosphate and potassium hydrogen phosphate, including the hydrated forms thereof.

Preferred 10. The process of the invention wherein the mixture comprises flupyrsulfuron-methyl.

Preferred 10A. The process of Preferred 10 wherein the mixture comprises at least about 75 equivalent % of inorganic base relative to flupyrsulfuron-methyl.

Preferred 10B. The process of Preferred 10 wherein the mixture comprises at least about 100 equivalent % of inorganic base relative to flupyrsulfuron-methyl.

Preferred 10C. The process of Preferred 10, 10A or 10B wherein the inorganic base comprises at least one base selected from sodium carbonate, sodium phosphate, sodium hydrogen phosphate, potassium carbonate, potassium phosphate and potassium hydrogen phosphate, including the hydrated forms thereof.

Preferred 11. The process of the invention wherein the mixture comprises flazasulfuron.

Preferred 11A. The process of Preferred 11 wherein the mixture comprises at least about 75 equivalent % of inorganic base relative to flazasulfuron.

Preferred 11B. The process of Preferred 11 wherein the mixture comprises at least about 100 equivalent % of inorganic base relative to flazasulfuron.

Preferred 11C. The process of Preferred 11, 11A or 11B wherein the inorganic base comprises at least one base selected from sodium carbonate, sodium phosphate, sodium hydrogen phosphate, potassium carbonate, potassium phosphate and potassium hydrogen phosphate, including the hydrated forms thereof.

Preferred 12. The process of the invention wherein the mixture comprises foramsulfuron.

Preferred 12A. The process of Preferred 12 wherein the mixture comprises at least about 75 equivalent % of inorganic base relative to foramsulfuron.

Preferred 12B. The process of Preferred 12 wherein the mixture comprises at least about 100 equivalent % of inorganic base relative to foramsulfuron.

Preferred 12C. The process of Preferred 12, 12A or 12B wherein the inorganic base comprises at least one base selected from sodium carbonate, sodium phosphate, sodium hydrogen phosphate, potassium carbonate, potassium phosphate and potassium hydrogen phosphate, including the hydrated forms thereof.

Preferred 13. The process of the invention wherein the mixture comprises halosulfuron-methyl.

Preferred 13A. The process of Preferred 13 wherein the mixture comprises at least about 75 equivalent % of inorganic base relative to halosulfuron-methyl.

Preferred 13B. The process of Preferred 13 wherein the mixture comprises at least about 100 equivalent % of inorganic base relative to halosulfuron-methyl.

Preferred 13C. The process of Preferred 13, 13A or 13B wherein the inorganic base comprises at least one base selected from sodium carbonate, sodium hydrogen carbonate, sodium phosphate, sodium hydrogen phosphate, potassium carbonate, potassium hydrogen carbonate, potassium phosphate and potassium hydrogen phosphate, including the hydrated forms thereof.

Preferred 14. The process of the invention wherein the mixture comprises imazosulfuron.

Preferred 14A. The process of Preferred 14 wherein the mixture comprises at least about 75 equivalent % of inorganic base relative to imazosulfuron.

Preferred 14B. The process of Preferred 14 wherein the mixture comprises at least about 100 equivalent % of inorganic base relative to imazosulfuron.

Preferred 14C. The process of Preferred 14, 14A or 14B wherein the inorganic base comprises at least one base selected from sodium carbonate, sodium hydrogen carbonate, sodium phosphate, sodium hydrogen phosphate, potassium carbonate, potassium hydrogen carbonate, potassium phosphate and potassium hydrogen phosphate, including the hydrated forms thereof.

Preferred 15. The process of the invention wherein the mixture comprises iodosulfuron-methyl.

Preferred 15A. The process of Preferred 15 wherein the mixture comprises at least about 75 equivalent % of inorganic base relative to iodosulfuron-methyl.

Preferred 15B. The process of Preferred 15 wherein the mixture comprises at least about 100 equivalent % of inorganic base relative to iodosulfuron-methyl.

Preferred 15C. The process of Preferred 15, 15A or 15B wherein the inorganic base comprises at least one base selected from sodium carbonate, sodium hydrogen carbonate, sodium phosphate, sodium hydrogen phosphate, potassium carbonate, potassium hydrogen carbonate, potassium phosphate and potassium hydrogen phosphate, including the hydrated forms thereof.

Preferred 16. The process of the invention wherein the mixture comprises mesosulfuron-methyl.

Preferred 16A. The process of Preferred 16 wherein the mixture comprises at least about 75 equivalent % of inorganic base relative to mesosulfuron-methyl.

Preferred 16B. The process of Preferred 16 wherein the mixture comprises at least about 100 equivalent % of inorganic base relative to mesosulfuron-methyl.

Preferred 16C. The process of Preferred 16, 16A or 16B wherein the inorganic base comprises at least one base selected from sodium carbonate, sodium phosphate, sodium hydrogen phosphate, potassium carbonate, potassium phosphate and potassium hydrogen phosphate, including the hydrated forms thereof.

Preferred 17. The process of the invention wherein the mixture comprises metsulfuron-methyl.

Preferred 17A. The process of Preferred 17 wherein the mixture comprises at least about 75 equivalent % of inorganic base relative to metsulfuron-methyl.

Preferred 17B. The process of Preferred 17 wherein the mixture comprises at least about 100 equivalent % of inorganic base relative to metsulfuron-methyl.

Preferred 17C. The process of Preferred 17, 17A or 17B wherein the inorganic base comprises at least one base selected from sodium carbonate, sodium hydrogen carbonate, sodium phosphate, sodium hydrogen phosphate, potassium carbonate, potassium hydrogen carbonate, potassium phosphate and potassium hydrogen phosphate, including the hydrated forms thereof.

Preferred 18. The process of the invention wherein the mixture comprises nicosulfuron.

Preferred 18A. The process of Preferred 18 wherein the mixture comprises at least about 75 equivalent % of inorganic base relative to nicosulfuron.

Preferred 18B. The process of Preferred 18 wherein the mixture comprises at least about 100 equivalent % of inorganic base relative to nicosulfuron.

Preferred 18C. The process of Preferred 18, 18A or 18B wherein the inorganic base comprises at least one base selected from sodium carbonate, sodium phosphate, sodium hydrogen phosphate, potassium carbonate, potassium phosphate and potassium hydrogen phosphate, including the hydrated forms thereof.

Preferred 19. The process of the invention wherein the mixture comprises oxasulfuron.

Preferred 19A. The process of Preferred 19 wherein the mixture comprises at least about 75 equivalent % of inorganic base relative to oxasulfuron.

Preferred 19B. The process of Preferred 19 wherein the mixture comprises at least about 100 equivalent % of inorganic base relative to oxasulfuron.

Preferred 19C. The process of Preferred 19, 19A or 19B wherein the inorganic base comprises at least one base selected from sodium carbonate, sodium phosphate, sodium hydrogen phosphate, potassium carbonate, potassium phosphate and potassium hydrogen phosphate, including the hydrated forms thereof.

Preferred 20. The process of the invention wherein the mixture comprises primisulfuron-methyl.

Preferred 20A. The process of Preferred 20 wherein the mixture comprises at least about 75 equivalent % of inorganic base relative to primisulfuron-methyl.

Preferred 20B. The process of Preferred 20 wherein the mixture comprises at least about 100 equivalent % of inorganic base relative to primisulfuron-methyl.

Preferred 20C. The process of Preferred 20, 20A or 20B wherein the inorganic base comprises at least one base selected from sodium carbonate, sodium hydrogen carbonate, sodium phosphate, sodium hydrogen phosphate, potassium carbonate, potassium hydrogen carbonate, potassium phosphate and potassium hydrogen phosphate, including the hydrated forms thereof.

Preferred 21. The process of the invention wherein the mixture comprises prosulfuron.

Preferred 21A. The process of Preferred 21 wherein the mixture comprises at least about 75 equivalent % of inorganic base relative to prosulfuron.

Preferred 21B. The process of Preferred 21 wherein the mixture comprises at least about 100 equivalent % of inorganic base relative to prosulfuron.

Preferred 21C. The process of Preferred 21, 21A or 21B wherein the inorganic base comprises at least one base selected from sodium carbonate, sodium hydrogen carbonate, sodium phosphate, sodium hydrogen phosphate, potassium carbonate, potassium hydrogen carbonate, potassium phosphate and potassium hydrogen phosphate, including the hydrated forms thereof.

Preferred 22. The process of the invention wherein the mixture comprises pyrazosulfuron-ethyl.

Preferred 22A. The process of Preferred 22 wherein the mixture comprises at least about 75 equivalent % of inorganic base relative to pyrazosulfuron-ethyl.

Preferred 22B. The process of Preferred 22 wherein the mixture comprises at least about 100 equivalent % of inorganic base relative to pyrazosulfuron-ethyl.

Preferred 22C. The process of Preferred 22, 22A or 22B wherein the inorganic base comprises at least one base selected from sodium carbonate, sodium hydrogen carbonate, sodium phosphate, sodium hydrogen phosphate, potassium carbonate, potassium hydrogen carbonate, potassium phosphate and potassium hydrogen phosphate, including the hydrated forms thereof.

Preferred 23. The process of the invention wherein the mixture comprises rimsulfuron.

Preferred 23A. The process of Preferred 23 wherein the mixture comprises at least about 75 equivalent % of inorganic base relative to rimsulfuron.

Preferred 23B. The process of Preferred 23 wherein the mixture comprises at least about 100 equivalent % of inorganic base relative to rimsulfuron.

Preferred 23C. The process of Preferred 23, 23A or 23B wherein the inorganic base comprises at least one base selected from sodium carbonate, sodium hydrogen carbonate, sodium phosphate, sodium hydrogen phosphate, potassium carbonate, potassium hydrogen carbonate, potassium phosphate and potassium hydrogen phosphate, including the hydrated forms thereof.

Preferred 24. The process of the invention wherein the mixture comprises sulfometuron-methyl.

Preferred 24A. The process of Preferred 24 wherein the mixture comprises at least about 100 equivalent % of inorganic base relative to sulfometuron-methyl.

Preferred 24B. The process of Preferred 24 or 24A wherein the inorganic base comprises at least one base selected from sodium carbonate, sodium phosphate, potassium carbonate and potassium phosphate, including the hydrated forms thereof.

Preferred 25. The process of the invention wherein the mixture comprises sulfosulfuron.

Preferred 25A. The process of Preferred 25 wherein the mixture comprises at least about 75 equivalent % of inorganic base relative to sulfosulfuron.

Preferred 25B. The process of Preferred 25 wherein the mixture comprises at least about 100 equivalent % of inorganic base relative to sulfosulfuron.

Preferred 25C. The process of Preferred 25, 25A or 25B wherein the inorganic base comprises at least one base selected from sodium carbonate, sodium hydrogen carbonate, sodium phosphate, sodium hydrogen phosphate, potassium carbonate, potassium hydrogen carbonate, potassium phosphate and potassium hydrogen phosphate, including the hydrated forms thereof.

Preferred 26. The process of the invention wherein the mixture comprises thifensulfuron-methyl.

Preferred 26A. The process of Preferred 26 wherein the mixture comprises at least about 75 equivalent % of inorganic base relative to thifensulfuron-methyl.

Preferred 26B. The process of Preferred 26 wherein the mixture comprises at least about 100 equivalent % of inorganic base relative to thifensulfuron-methyl.

Preferred 26C. The process of Preferred 26, 26A or 26B wherein the inorganic base comprises at least one base selected from sodium carbonate, sodium hydrogen carbonate, sodium phosphate, sodium hydrogen phosphate, potassium carbonate, potassium hydrogen carbonate, potassium phosphate and potassium hydrogen phosphate, including the hydrated forms thereof.

Preferred 27. The process of the invention wherein the mixture comprises tribenuron-methyl.

Preferred 27A. The process of Preferred 27 wherein the mixture comprises at least about 75 equivalent % of inorganic base relative to tribenuron-methyl.

Preferred 27B. The process of Preferred 27 wherein the mixture comprises at least about 100 equivalent % of inorganic base relative to tribenuron-methyl.

Preferred 27C. The process of Preferred 27, 27A or 27B wherein the inorganic base comprises at least one base selected from sodium carbonate, sodium phosphate, sodium hydrogen phosphate, potassium carbonate, potassium phosphate and potassium hydrogen phosphate, including the hydrated forms thereof.

Preferred 28. The process of the invention wherein the mixture comprises trifloxysulfuron.

Preferred 28A. The process of Preferred 28 wherein the mixture comprises at least about 75 equivalent % of inorganic base relative to trifloxysulfuron.

Preferred 28B. The process of Preferred 28 wherein the mixture comprises at least about 100 equivalent % of inorganic base relative to trifloxysulfuron.

Preferred 28C. The process of Preferred 28, 28A or 28B wherein the inorganic base comprises at least one base selected from sodium carbonate, sodium phosphate, sodium hydrogen phosphate, potassium carbonate, potassium phosphate and potassium hydrogen phosphate, including the hydrated forms thereof.

Preferred 29. The process of the invention wherein the mixture comprises triflusulfuron-methyl.

Preferred 29A. The process of Preferred 29 wherein the mixture comprises at least about 75 equivalent % of inorganic base relative to triflusulfuron-methyl.

Preferred 29B. The process of Preferred 29 wherein the mixture comprises at least about 100 equivalent % of inorganic base relative to triflusulfuron-methyl.

Preferred 29C. The process of Preferred 29, 29A or 29B wherein the inorganic base comprises at least one base selected from sodium carbonate, sodium phosphate, sodium hydrogen phosphate, potassium carbonate, potassium phosphate and potassium hydrogen phosphate, including the hydrated forms thereof.

Preferred 30. The process of the invention wherein the mixture comprises tritosulfuron.

Preferred 30A. The process of Preferred 30 wherein the mixture comprises at least about 75 equivalent % of inorganic base relative to tritosulfuron.

Preferred 30B. The process of Preferred 30 wherein the mixture comprises at least about 100 equivalent % of inorganic base relative to tritosulfuron.

Preferred 30C. The process of Preferred 30, 30A or 30B wherein the inorganic base comprises at least one base selected from sodium carbonate, sodium hydrogen carbonate, sodium phosphate, sodium hydrogen phosphate, potassium carbonate, potassium hydrogen carbonate, potassium phosphate and potassium hydrogen phosphate, including the hydrated forms thereof.

Preferred 31. The process of the invention wherein the mixture comprises cloransulam-methyl.

Preferred 31A. The process of Preferred 31 wherein the mixture comprises at least about 75 equivalent % of inorganic base relative to cloransulam-methyl.

Preferred 31B. The process of Preferred 31 wherein the mixture comprises at least about 100 equivalent % of inorganic base relative to cloransulam-methyl.

Preferred 31C. The process of Preferred 31, 31A or 31B wherein the inorganic base comprises at least one base selected from sodium carbonate, sodium phosphate, sodium hydrogen phosphate, potassium carbonate, potassium phosphate and potassium hydrogen phosphate, including the hydrated forms thereof.

Preferred 32. The process of the invention wherein the mixture comprises diclosulam.

Preferred 32A. The process of Preferred 32 wherein the mixture comprises at least about 75 equivalent % of inorganic base relative to diclosulam.

Preferred 32B. The process of Preferred 32 wherein the mixture comprises at least about 100 equivalent % of inorganic base relative to diclosulam.

Preferred 32C. The process of Preferred 32, 32A or 32B wherein the inorganic base comprises at least one base selected from sodium carbonate, sodium hydrogen carbonate, sodium phosphate, sodium hydrogen phosphate, potassium carbonate, potassium hydrogen carbonate, potassium phosphate and potassium hydrogen phosphate, including the hydrated forms thereof.

Preferred 33. The process of the invention wherein the mixture comprises florasulam.

Preferred 33A. The process of Preferred 33 wherein the mixture comprises at least about 75 equivalent % of inorganic base relative to florasulam.

Preferred 33B. The process of Preferred 33 wherein the mixture comprises at least about 100 equivalent % of inorganic base relative to florasulam.

Preferred 33C. The process of Preferred 33, 33A or 33B wherein the inorganic base comprises at least one base selected from sodium carbonate, sodium phosphate, sodium hydrogen phosphate, potassium carbonate, potassium phosphate and potassium hydrogen phosphate, including the hydrated forms thereof.

Preferred 34. The process of the invention wherein the mixture comprises flumetsulam.

Preferred 34A. The process of Preferred 34 wherein the mixture comprises at least about 75 equivalent % of inorganic base relative to flumetsulam.

Preferred 34B. The process of Preferred 34 wherein the mixture comprises at least about 100 equivalent % of inorganic base relative to flumetsulam.

Preferred 34C. The process of Preferred 34, 34A or 34B wherein the inorganic base comprises at least one base selected from sodium carbonate, sodium phosphate, sodium hydrogen phosphate, potassium carbonate, potassium phosphate and potassium hydrogen phosphate, including the hydrated forms thereof.

Preferred 35. The process of the invention wherein the mixture comprises metosulam.

Preferred 35A. The process of Preferred 35 wherein the mixture comprises at least about 75 equivalent % of inorganic base relative to metosulam.

Preferred 35B. The process of Preferred 35 wherein the mixture comprises at least about 100 equivalent % of inorganic base relative to metosulam.

Preferred 35C. The process of Preferred 35, 35A or 35B wherein the inorganic base comprises at least one base selected from sodium carbonate, sodium phosphate, sodium hydrogen phosphate, potassium carbonate, potassium phosphate and potassium hydrogen phosphate, including the hydrated forms thereof.

Preferred 36. The process of the invention wherein the mixture comprises penoxsulam.

Preferred 36A. The process of Preferred 36 wherein the mixture comprises at least about 75 equivalent % of inorganic base relative to penoxsulam.

Preferred 36B. The process of Preferred 36 wherein the mixture comprises at least about 100 equivalent % of inorganic base relative to penoxsulam.

Preferred 36C. The process of Preferred 36, 36A or 36B wherein the inorganic base comprises at least one base selected from sodium carbonate, sodium phosphate, sodium hydrogen phosphate, potassium carbonate, potassium phosphate and potassium hydrogen phosphate, including the hydrated forms thereof.

Preferred compositions include those prepared by the preferred processes of the invention.

The mixture for extrusion according the process of this invention and the water-dispersible granular composition prepared therefrom may include other active ingredients besides sulfonamide herbicides. These other active ingredients may include herbicides, plant growth regulators, herbicide safeners, insecticides, insect antifeedants, miticides, nematocides, bactericides and fungicides. Most commonly, the other active ingredients will be herbicides or herbicide safeners. Examples of herbicides include acetochlor, acifluorfen, aclonifen, alachlor, alloxydim, ametryn, amicarbazone, amitrole, anilofos, asulam, atrazine, azafenidin, beflubutamid, benazolin, benfluralin, benfuresate, bensulide, bentazone, benzobicyclon, benzofenap, bifenox, bilanafos, bispyribac, bromacil, bromobutide, bromoxynil, butachlor, butafenacil, butamifos, butralin, butroxydim, butylate, cafenstrole, carbetamide, carfentrazone-ethyl, chloramben, chlorbromuron, chlorflurenol-methyl, chloridazon, chlorotoluron, chlorpropham, chlorthal-dimethyl, chlorthiamid, cinidonethyl, cinmethylin, clethodim, clodinafop-propargyl, clomazone, clomeprop, clopyralid, cumyluron, cyanazine, cycloate, cycloxydim, cyhalofop-butyl, 2,4-D, daimuron, 2,4-DB, dazomet, desmedipham, dicamba, dichlobenil, dichlorprop, diclofop-methyl, difenzoquat metilsulfate, diflufenican, diflufenzopyr, dimefuron, dimepiperate, dimethachlor, dimethametryn, dimethenamid, dimethipin, dinitramine, dinoterb, diphenamid, diquat dibromide, dithiopyr, diuron, endothal, EPTC, esprocarb, ethalfluralin, ethofumesate, etobenzanid, fenoxaprop-P-ethyl, fentrazamide, fenuron, flamprop-M, fluazifop-butyl, fluazifop-P-butyl, fluazolate, flucarbazone, fluchloralin, flufenacet, flumichlorac-pentyl, flumioxazin, fluometuron, fluoroglycofen-ethyl, fluridone, flurochloridone, fluroxypyr, flurtamone, fluthiacet-methyl, fomesafen, glufosinate, glyphosate, haloxyfop, hexazinone, imazamethabenz-methyl, imazamox, imazapic, imazapyr, imazaquin, imazethapyr, indanofan, ioxynil, isoproturon, isouron, isoxaben, isoxaflutole, isoxachlortole, lactofen, lenacil, linuron, MCPA, MCPB, mecoprop, mecoprop-P, mefenacet, mefluidide, mesotrione, metamitron, metazacilor, methabenzthiazuron, methyldymron, metobenzuron, metobromuron, metolachlor, S-metolachlor, metoxuron, metribuzin, molinate, monolinuron, naproanilide, napropamide, naptalam, neburon, norflurazon, orbencarb, oryzalin, oxadiargyl, oxadiazon, oxaziclomefone, oxyfluorfen, paraquat dichloride, pebulate, pendimethalin, pentanochlor, pentoxazone, phemnedipham, picloram, picolinafen, piperophos, pretilachlor, prodiamine, prometon, prometryn, propachlor, propanil, propaquizafop, propazine, propham, propisochlor, propyzamide, prosulfocarb, pyraflufen-ethyl, pyrazolynate, pyrazoxyfen, pyribenzoxim, pyributicarb, pyridate, pyriftalid, pyriminobac-methyl, pyrithiobac, quinclorac, quinmerac, quizalofop, quizalofop-P, sethoxydim, siduron, simazine, simetryn, sulcotrione, sulfentrazone, 2,3,6-TBA, tebutam, tebuthiuron, tepraloxydim, terbacil, terbumeton, terbuthylazine, terbutryn, thenylchlor, thiazopyr, thiobencarb, tiocarbazil, tralkoxydim, triallate, triaziflam, triclopyr, trietazine, trifluralin and vernolate. Illustrative herbicide safeners include benoxacor, BCS (1-bromo-4-[(chloromethyl)sulfonyl]benzene), cloquintocet-mexyl, cyometrinil, dichlormid, 2-(dichloromethyl)-2-methyl-1,3-dioxolane (MG 191), fenchlorazole-ethyl, fenclorim, flurazole, fluxofenim, furilazole, isoxadifen-ethyl, mefenpyr-ethyl, methoxyphenone ((4-methoxy-3-methylphenyl)(3-methylphenyl)-methanone), naphthalic anhydride and oxabetrinil. Of note are compositions where the mole ratio of other active ingredients to sulfonamide herbicides is between 1:100 and 100:1.

Of note are processes of this invention wherein the mixture for extrusion comprises sulfometuron-methyl and a base comprising sodium phosphate, or comprises thifensulfuron-methyl and a base comprising sodium carbonate, or comprises tribenuron-methyl and a base comprising sodium carbonate. Illustrating a combination of inorganic bases, of further note is a process of this invention wherein the mixture for extrusion comprises tribenuron-methyl and a base comprising sodium carbonate and sodium phosphate. Also of note are paste-extruded sulfonamide herbicide compositions prepared by the processes of note.

The mixture for extrusion according to the process of this invention may optionally contain up to 95%, typically from 5 to 70% and often from 20 to 50% by weight on a water-free basis of additives selected from wetting agents, dispersants, lubricants, anticaking agents, chemical stabilizers and diluents. One skilled in the art understands the purpose and selection of these additives.

Wetting agents include but are not limited to alkyl sulfosuccinates, laurates, alkyl sulfate and phosphate esters, acetylenic diols, ethoxyfluorinated alcohols, ethoxylated silicones, alkyl phenol ethoxylates, benzene sulfonates, alkyl-substituted benzene sulfonates, alkyl α-olefin sulfonates, napthalene sulfonates, alkyl-substituted napthalene sulfonates, condensates of naphthalene sulfonates and alkyl-substituted napthalene sulfonates with formaldehyde, and alcohol ethoxylates. Of note are compositions comprising up to 10% (e.g., from 0.1 to 5%) by weight of wetting agent on a water-free basis. Compositions prepared according to the process of this invention can comprise considerably greater amounts of wetting agents (e.g., up to about 90 weight %) if the amounts of active ingredient and base are correspondingly limited to accommodate the amount of wetting agent.

Dispersants include but are not limited to sodium, calcium and ammonium salts of ligninsulfonates (optionally polyethoxylated); sodium and ammonium salts of maleic anhydride copolymers; sodium salts of condensed phenolsulfonic acid; and napthalene sulfonate-formaldehyde condensates.

Of note are compositions comprising up to 10% (e.g., from 0.1 to 5%) by weight of dispersant on a water-free basis. Ligninsulfonates such as sodium lignosulfonate are particularly useful for the process and composition of the invention.

Lubricants include but are not limited to polyvinylpyrrolidone, polyvinylalcohol and polyethylene oxide. They have a median molecular weight greater than 50,000, a melt flow temperature of at least 98° C., and do not behave as surfactants. Polyethylene oxide is preferred. Of note are compositions comprising up to 3% (e.g., from 0.01 to 2%) by weight of lubricant on a water-free basis. Higher levels are less desirable, because they can slow the disintegration rate of the granule.

Anticaking agents prevent clumping of granules, which could occur during storage under hot warehouse conditions. Inorganic bases such as sodium and ammonium phosphates used to provide base equivalents may also help prevent clumping of granules. As referred to herein, the term "anticaking agent" does not include inorganic bases having conjugate acid $pK_a$s at least 2.1 units greater than the highest $pK_a$ of the sulfonamide free acid component. Anticaking agents include, but are not limited to, sodium and ammonium phosphates not having conjugate acid $pK_a$s at least 2.1 units greater than the highest $pK_a$ of the sulfonamide free acid component (e.g., sodium dihydrogen phosphate), sodium acetate, magnesium hydroxide (all optionally hydrates), anhydrous calcium chloride, molecular sieves, sodium alkylsulfosuccinates, calcium and barium oxides. Of note are compositions comprising up to 10% (e.g., from 0.1 to 5%) by weight of anticaking agent on a water-free basis.

Chemical stabilizers prevent decomposition of active ingredient during storage. Inorganic bases such as lithium, sodium and potassium phosphates used to provide base equivalents may also help prevent decomposition of active ingredient. As referred to herein, the term "chemical stabilizer" does not include inorganic bases having conjugate acid $pK_a$s at least 2.1 units greater than the highest $pK_a$ of the sulfonamide free acid component. Chemical stabilizers include, but are not limited to, lithium, sodium and potassium phosphates not having conjugate acid $pK_a$s at least 2.1 units greater than the highest $pK_a$ of the sulfonamide free acid component (e.g., sodium dihydrogen phosphate); sulfates of alkaline earth metals and transition metals such as magnesium, zinc, aluminum and iron; calcium chloride and oxide; and boric anhydride. Of note are compositions comprising up to 10% (e.g., from 0.1 to 5%) by weight of chemical stabilizer on a water-free basis.

Diluents, which include but are not limited to binders and fillers, may be water-soluble or water-insoluble. Inorganic bases such as alkali metal phosphates used to provide base equivalents may also act as binders or fillers. As referred to herein, the term "diluent" does not include inorganic bases having conjugate acid $pK_a$s at least 2.1 units greater than the highest $pK_a$ of the sulfonamide free acid component. The water-soluble diluents may be, for example, salts or carbohydrates which dissolve rapidly in water; non-limiting examples include alkali metal phosphates not having conjugate acid $pK_a$s at least 2.1 units greater than the highest $pK_a$ of the sulfonamide free acid component (e.g., sodium dihydrogen phosphate), alkaline earth phosphates, sulfates of sodium, potassium, magnesium and zinc, sodium and potassium chloride, sorbitol, sodium benzoate, lactose and sucrose. Water-insoluble diluents include, but are not limited to clays, synthetic and diatomaceous silicas, calcium and magnesium silicates, titanium dioxide, aluminum, calcium and zinc oxide, calcium and magnesium carbonate, sodium, potassium, calcium and barium sulfate, and charcoal. Water-soluble diluents are preferred. Of note are compositions comprising up to 85% (e.g., from 5 to 70%) by weight of diluent on a water-free basis. Preferred as diluents in the process and composition of the invention are saccharides, including monosaccharides (e.g., glucose) and disaccharides (e.g., lactose, sucrose), in the amount of from about 0.5 to about 50% by weight on a water-free basis. Disaccharides such as lactose and sucrose are particularly preferred.

In preparing the mixture for extrusion, the other components of the mixture are typically blended to form a homogeneous composition before addition of water to make the mixture into an extrudable paste. Of note is a solid composition (e.g., a powder) comprising from 2 to 90% by weight on a water-free basis of one or more active ingredients comprising at least one sulfonamide herbicide free acid; from 0.5 to 94% by weight on a water-free basis of a saccharide, preferably a disaccharide such as lactose or sucrose; from 1 to 20% by weight on a water-free basis of surfactant component preferably comprising a dispersant, for example a ligninsulfonate dispersant (e.g., sodium lignosulfonate), and optionally a wetting agent, for example a lauryl sulfate salt (e.g., sodium lauryl sulfate); and at least about 50 equivalent % of base selected from inorganic base equivalents having conjugate acid $pK_a$s at least 2.1 units greater than the highest $pK_a$ of the sulfonamide herbicide free acid component; wherein at least 10% of the sulfonamide herbicide content in the composition is in free acid form. Said saccharide-containing solid composition may optionally comprise additional ingredients; the sum of the weight % of all the ingredients in said composition totaling 100% of a water-free basis Unmoistened homogeneous mixtures can be milled as necessary to a form a powder for extrusion. The sizes of particles in the powder for extrusion can vary considerably and still provide according to the process of this invention an extruded sulfonamide composition having good dispersibility, herbicidal efficacy and spray equipment clean-out properties. Typically after milling, the powder for extrusion has a mean particle size of less than about 60 microns (μm), and at least 90% of the particles are less than about 300 microns, wherein particle size is the equivalent spherical diameter of the particle, i.e. the diameter of a sphere enclosing the same volume as the particle. Milling using such equipment as hammer mills typically can provide considerably finer powders, which may increase the rate of dispersion or improve other properties of the sulfonamide compositions prepared by the present process. Mean particle size is the volume moment mean, also known as the volume mean and the De Broucker mean, for the particles in the powder for extrusion. With reference to particle size distribution of the powder, percentages of particles are also on a volume basis (e.g., "at least 90% of the particles are less than about 300 microns" means that at least 90% of the aggregate volume of particles consists of particles having equivalent spherical diameters of less than about 300 microns). The principles of particle size analysis are well known to those skilled in the art; for a technical paper providing a summary, see A. Rawle, "Basic Principles of Particle Size Analysis" (document MRK034 published by Malvern Instruments Ltd., Malvern, Worcestershire, UK). Volume distributions of particles in powders can be conveniently measured by such techniques as Low Angle Laser Light Scattering (also known as LALLS and Laser Diffraction), which relies on the fact that diffraction angle is inversely proportional to particle size. Commercially available instruments suitable for analyzing using LALLS the volume distributions of particles in powders include the Mastersizer 2000 (Malvern Instruments). Preferred is the process of this invention in which the powder for extrusion has a mean particle size of less than about 30 microns, more preferably less than about 20 microns and most preferably less than about 15 microns, and in which at least 90% of the particles are less than about 100 microns, more preferably less than about 40 microns and most preferably less than about 30 microns. Alternatively, milling of components may be done separately prior to incorporation into the mixture. In some cases, it is sufficient to mill only the water insoluble components. Suitable mills include, but are not limited to, lab-scale high-speed rotary mills, such as a Techmar® A10 Analytical Mill, and commercial-scale hammer mills and air classifying mills, such as those manufactured by Hosokawa Micron Powder Systems, Summit, N.J.

To make the mixture suitable for extrusion, water is added to form an extrudable paste. The mixture of dry components is typically added to a low to moderate shear mixer, or kneader, wetted with water and mixed until an extrudable paste is obtained. Water may be added either as a spray or as a stream. Typically, 5 to 50% water based on the weight of dry component mixture (i.e. 5 to 50 parts of water to 100 parts by weight of dry component mixture) is required to produce an extrudable paste. Alternatively, water-soluble ingredients may be added to the water. Water-soluble ingredients that may be added include, for example but not limitation, other volatile solvents such as lower molecular weight alcohols (e.g., methanol, ethanol and isopropanol) as well as nonvolatile formulating ingredients described above (e.g., wetting agents, dispersants, lubricants, anticaking agents, chemical stabilizers and diluents) that are water soluble. Also, part or all of the inorganic base equivalents in the mixture can be first dissolved in the water. Typically the added water does not contain water-soluble ingredients other than impurities commonly found in tap (i.e. potable) water. Suitable mixers include, but are not limited to, food processors, sigma arm mixers (such as a "Kneadermaster" manufactured by The Patterson Foundry & Machine Co., East Liverpool, Ohio), pug mixers and continuous kneaders (such as those available from LCI Corporation, Charlotte, N.C.).

Extrusion is accomplished by passing the paste through a paste extruder to produce extrudate (a wet extruded strand). Examples of paste extruders include, but are not limited to, basket extruders, radial extruders and dome extruders; such as available from LCI Corporation, Charlotte, N.C. The extruder is fitted with a die, or screen, with hole diameters typically from 0.3 to 3 mm, preferably 0.5 to 1.5 mm and most preferably 0.7 to 1.0 mm.

The extrudate is then dried. A wide variety of drying methods can be used to dry the extrudate. Conventional drying methods include tray, rotary, fluidized bed and vibrating fluidized bed. Drying methods that subject the extrudate to vibration, tumbling or other forms of agitation will also serve to break the extruded strand into shorter lengths and ultimately into granules that can be dispensed by volumetric measurement. Fluidized bed drying is preferred, as fluidization will increase fracture of the drying extruded strand by impact into discrete granules. Most preferred is vibrating fluidized bed drying. Drying to moisture levels less than 5% (preferably less than 3%) as measured by a moisture balance, such as available from Mettler, Inc., Toledo, Ohio, produces hardened granules without tack. Hardened, non-tacky granules are preferred, because they have reduced tendency to agglomerate. Drying temperatures greater than about 40° C., preferably at least 60° C. but not exceeding 110° C. and typically not exceeding 90° C., efficiently produce the required moisture levels.

Prior to packaging and use, the dried extruded granules are typically sifted to remove fines and any agglomerated chunks, as well as possibly break the extruded granules into shorter lengths. Accordingly, the process of this invention may further comprise a step of sifting the dried extrudate. Compositions of granules with lengths suitable for dispensing by volumetric measurement can be obtained by breaking the dried granules using sifting to obtain length distributions from about 0.3 to about 7 mm, preferably from about 0.5 to about 5 mm and most preferably from about 0.7 to about 4 mm. Alternatively the dried granules can be broken using a rotary sifter as described in U.S. Pat. No. 6,270,025 to produce length distributions that are especially suitable for preparing homogeneous blends as described in U.S. Pat. No. 6,022,552.

Besides having significantly improved spray tank clean out properties, formulations prepared from mixtures containing at least about 50 equivalent % of a base according to the process of this invention have also been discovered to provide substantially better control of weeds under certain circumstances than comparison formulations prepared from mixtures containing lesser amounts or no base. Because weed control has a limit of 100%, better weed control by formulations of this invention are most apt to be realized under circumstances where said comparison formulations provide much less than 100% control. These circumstances include treatment of hard-to-control weed species, which may be only suppressed instead of efficiently controlled by said comparison formulations. The improved herbicidal efficacy of formulations of this invention may also be realized in controlling otherwise relatively easy-to-control weed species at low application rates for which said comparison formulations provide only suppression. Other circumstances where formulations of this invention may provide significantly improved weed control include applications using relatively small spray volumes. Formulations of the present invention may obviate need to add to the spray liquid supplementary surfactants besides those included in the formulation, although adding such surfactants may also benefit weed control by formulations of the present invention.

Without further elaboration, it is believed that one skilled in the art using the preceding description can utilize the present invention to its fullest extent. The following Examples are, therefore, to be construed as merely illustrative and not limiting of the disclosure in any way whatsoever.

ANALYTICAL EXAMPLES

Analytical Example 1

Illustrative Procedure for Determining $pK_a$ of a Sulfonamide Herbicide

A stock buffer solution is prepared by dissolving sodium acetate trihydrate (6.8 g), sodium phosphate dodecahydrate (19.0 g) and sodium borate decahydrate (19.1 g) in highly purified water (500 mL). This stock buffer solution is typically diluted 100-fold with highly purified water to give a 0.001 M test buffer solution having a pH between pH 9 and pH 10. If necessary, a stronger concentration of the buffer can be prepared. A stock solution of the sulfonamide herbicide free acid is prepared in an organic solvent, preferably a solvent miscible with water such as acetone. The concentration of the stock solution should not exceed the lesser of 1 M or half the saturation concentration for the organic solvent used.

A UV/visible light spectrophotometer equipped with temperature control capable of maintaining temperature at the test temperature (e.g., 20° C.) is used to record spectra for the sulfonamide at various pHs. The 0.001 M test buffer solution is used as a blank. Spectra are recorded for aliquots of the sulfonamide stock solution added to a hydrochloric acid solution (pH≦2) and sodium hydroxide solution (pH≧10), respectively. The optimal analytical wavelength, where the acidic and basic (salt) forms of the sulfonamide differ appreciably in absorbance from one another is noted and used for the subsequent analysis. An aliquot of the stock sulfonamide solution is added to a flask and the solvent evaporated under nitrogen. Buffer solution (0.001 M, 100 mL) is added to the flask, and the mixture is magnetically stirred to form the test solution. The pH is recorded using a calibrated pH meter capable of resolving differences of 0.1 pH units or less. The pH of the test solution is adjusted to approximately pH 2 using hydrochloric acid, and then sodium hydroxide solution is added in increments to obtain about 0.5 or less pH-units of change per increment up to pH of 10 to 12, and the UV/visible absorbance is recorded as a function of change in pH at the analytical wavelength. Regression analysis based on a non-linear, least-squares model for a plot of absorbance versus pH is performed to determine the pH at which the sulfonamide free acid and sulfonamide salt are present in equimolar amounts; this pH is the $pK_a$ of the sulfonamide. The test is preferably replicated to ensure accuracy.

Analytical Example 2

Illustrative Procedure for Determining Solubility of a Sulfonamide Herbicide in pH 7 Buffer A stock pH 7 buffer solution is prepared by adding aqueous sodium hydroxide solution (0.1 M, 145 mL) to aqueous potassium dihydrogen phosphate solution (0.1 M, 250 mL), and then adding sufficient distilled water to adjust the final volume to 500 mL. At least 1 times up to about 5 times the amount of sulfonamide needed for saturation is added to a mixing vessel containing stock buffer solution at the test temperature (e.g., 20° C.). The mixture is magnetically stirred in the dark while being maintained at the test temperature. Samples are periodically removed for analysis. The samples are centrifuged using a high speed, temperature-controlled centrifuge at the test temperature for about 20 minutes at ≧12000 G to remove suspended particles. An aliquot of each supernatant is taken for analysis.

The concentration of sulfonamide in the supernatant is determined by a high pressure liquid chromatography (HPLC) method suitable for the particular sulfonamide. Typically the HPLC method will use a reversed phase chromatography column and UV detection. The method should include development of best-fit calibration curves based on at least three standards using linear regression analysis. Also, the pH of the supernatant is measured using a calibrated pH meter capable of resolving differences of 0.1 pH units or less to verify that the pH is 7. Samples are successively withdrawn from the mixing vessel and analyzed until three successive samples show little or no variation in concentration. The test is preferably replicated to ensure accuracy.

FORMULATION PROCESS EXAMPLES

Formulations were prepared by combining ingredients in the indicated percentages to make from 20 to 50 grams of unmoistened mixture. Unless otherwise noted, formulations contained 50% of sulfonamide herbicide, 0.5% Supralate® ME Dry (sodium lauryl sulfate, marketed by Witco Inc., Greenwich, Conn.), 5% Reax® 88B (sodium lignosulfonate, marketed by Westvaco Corp., N. Charleston Heights, S.C.), and an inorganic base at an amount to give the indicated equivalent of base (relative to the sulfonamide herbicide) in the final composition. The balance of the formulation composition was sucrose and/or lactose monohydrate. The mixture was blended and milled in a high-speed rotary mill. The milled mixture (from 10 to 15 g) and water (from 2 to 5 mL) were combined using as mixer the rotary mill at low speed to form a paste, which was then extruded through a 1.0 mm die. The wet extrudate was dried at 70° C. in a vacuum oven and then sifted through 0.71-2 mm screens to obtain the product granules. The compositions of the example formulations are summarized in Table 1.

lation, commercially available from Syngenta, Basil, Switzerland) was added. The mixture was then stirred for an additional 2 minutes, whereupon the resulting dispersion was dispensed in three 100-mL aliquots to 4-oz (118-mL) polyethylene bottles. The bottles were capped, inverted twice and allowed to stand overnight.

After standing overnight, each individual bottle was inverted twice and the liquid contents were then poured out. Tap water (10 mL) was added and the bottle was inverted until all sediment was re-suspended, whereupon the contents were

TABLE 1

Summary of Example Formulations

| Ex. | Sulfonamide herbicide ingredient | Sulfonamide amt. (%) | Supralate ME (%) | Reax 88B (%) | Sucrose (%) | Lactose (*) (%) | Base ingredient | Base (%) |
|---|---|---|---|---|---|---|---|---|
| 1 | Thifensulfuron-methyl | 50.0 | 0.5 | 5.0 | 1.0 | 43.5 | None | — |
| 2 | Thifensulfuron-methyl | 50.0 | 0.5 | 5.0 | 1.0 | 34.5 | $Na_2HPO_4$ | 9.0 |
| 3 | Thifensulfuron-methyl | 50.0 | 0.5 | 5.0 | 1.0 | 6.5 | $Na_2HPO_4$ | 37.0 |
| 4 | Thifensulfuron-methyl | 50.0 | 0.5 | 5.0 | 1.0 | 36.5 | $K_3PO_4$ | 7.0 |
| 5 | Thifensulfuron-methyl | 50.0 | 0.5 | 5.0 | 1.0 | 16.5 | $K_3PO_4$ | 27.0 |
| 6 | Thifensulfuron-methyl | 50.0 | 0.5 | 5.0 | 1.0 | 40.1 | $Na_2CO_3$ | 3.4 |
| 7 | Thifensulfuron-methyl | 50.0 | 0.5 | 5.0 | 1.0 | 29.5 | $Na_2CO_3$ | 14.0 |
| 8 | Thifensulfuron-methyl | 50.0 | 0.5 | 5.0 | 1.0 | 36.5 | $KHCO_3$ | 7.0 |
| 9 | Thifensulfuron-methyl | 50.0 | 0.5 | 5.0 | 1.0 | 17.5 | $KHCO_3$ | 26.0 |
| 10 | Sulfometuron-methyl | 50.0 | 0.5 | 5.0 | 3.0 | 41.5 | None | — |
| 11 | Sulfometuron-methyl | 50.0 | 0.5 | 5.0 | 3.0 | 38.6 | $Na_3PO_4$ (**) | 2.9 |
| 12 | Sulfometuron-methyl | 50.0 | 0.5 | 5.0 | 3.0 | 35.9 | $Na_3PO_4$ (**) | 5.6 |
| 13 | Sulfometuron-methyl | 50.0 | 0.5 | 5.0 | 3.0 | 30.1 | $Na_3PO_4$ (**) | 11.4 |
| 14 | Sulfometuron-methyl | 50.0 | 0.5 | 5.0 | 3.0 | 19.1 | $Na_3PO_4$ (**) | 22.4 |
| 15 | Sulfometuron-methyl | 36.5 | 0.4 | 3.6 | 2.2 | 24.5 | $Na_3PO_4$ (**) | 32.8 |
| 16 | Sulfometuron-methyl | 50.0 | 0.5 | 4.0 | 0.0 | 0.5 | $Na_3PO_4$ | 45.0 |
| 17 | Bensulfuron-methyl | 50.0 | 0.5 | 5.0 | 0.0 | 44.5 | None | — |
| 18 | Bensulfuron-methyl | 50.0 | 0.5 | 5.0 | 0.0 | 41.1 | $Na_2CO_3$ | 3.4 |
| 19 | Bensulfuron-methyl | 50.0 | 0.5 | 5.0 | 0.0 | 37.8 | $Na_2CO_3$ | 6.7 |
| 20 | Bensulfuron-methyl | 50.0 | 0.5 | 5.0 | 0.0 | 31.5 | $Na_2CO_3$ | 13.0 |
| 21 | Bensulfuron-methyl | 50.0 | 0.5 | 5.0 | 0.0 | 18.5 | $Na_2CO_3$ | 26.0 |
| 22 | Tribenuron-methyl | 50.0 | 0.5 | 5.0 | 0.0 | 44.5 | None | — |
| 23 | Tribenuron-methyl | 50.0 | 0.5 | 5.0 | 0.0 | 37.8 | $Na_2CO_3$ | 6.7 |
| 24 | Tribenuron-methyl | 50.0 | 0.5 | 5.0 | 0.0 | 18.0 | $Na_2CO_3$ | 26.5 |

(*) Weight percentage also includes water of hydration and technical impurities in the formulations.
(**) $Na_3PO_4$ was added in the form of the dodecahydrate, but the listed amount is calculated based on the anhydrous equivalent.

The granular compositions were evaluated by the following clean-out test procedure that determines the sulfonamide herbicide residue that could potentially remain in organic deposits in a spray tank.

Laboratory Clean-Out Test Procedure

The test was conducted by dispersing in water a sample of the granular composition to produce a concentration that is normally used when applying the herbicide: 600 ppm for thifensulfuron-methyl and 350 ppm for sulfometuron-methyl, bensulfuron-methyl and tribenuron-methyl. The appropriate amount of the granules was added to tap water (300 mL) in a 400-mL beaker and magnetically stirred for 2 minutes. After stirring, Tilt® 250 (1.5 mL, propiconazole formupoured out. Tap water (100 mL) was added and the bottle was inverted twice and then allowed to stand undisturbed for 10 minutes. The bottle was inverted twice more and the contents were poured put. Acetonitrile (10 mL) was added to the bottle to extract any remaining material. The acetonitrile solution was analyzed by reversed-phase liquid chromatography with UV detection. The cleanout rating (the concentration of sulfonamide herbicide in the acetonitrile solution) is reported in ppm in Table 2 below. Lower cleanout ratings indicate more effective cleanout compared to higher ratings. The clean-out test was repeated twice for formulation examples 1, 10 and 17, which contained no base, and the two sets of results are separately listed.

TABLE 2

Summary of Formulations Evaluated Using Clean-Out Test

| Ex. | Sulfonamide herbicide ingredient | Sulfonamide amt. (%) | Base ingredient | Base (%) | Approx. Equivalent % Base Relative to S.U. | Cleanout Rating (as ppm S.U.) |
|---|---|---|---|---|---|---|
| 1 | Thifensulfuron-methyl | 50.0 | None | — | 0 | 203, 150 |
| 2 | Thifensulfuron-methyl | 50.0 | $Na_2HPO_4$ | 9.0 | 49 | 2 |
| 3 | Thifensulfuron-methyl | 50.0 | $Na_2HPO_4$ | 37.0 | 202 | 0 |
| 4 | Thifensulfuron-methyl | 50.0 | $K_3PO_4$ | 7.0 | 51 | 66 |
| 5 | Thifensulfuron-methyl | 50.0 | $K_3PO_4$ | 27.0 | 197 | 4 |
| 6 | Thifensulfuron-methyl | 50.0 | $Na_2CO_3$ | 3.4 | 50 | 9 |

TABLE 2-continued

Summary of Formulations Evaluated Using Clean-Out Test

| Ex. | Sulfonamide herbicide ingredient | Sulfonamide amt. (%) | Base ingredient | Base (%) | Approx. Equivalent % Base Relative to S.U. | Cleanout Rating (as ppm S.U.) |
|---|---|---|---|---|---|---|
| 7 | Thifensulfuron-methyl | 50.0 | Na$_2$CO$_3$ | 14.0 | 204 | 0 |
| 8 | Thifensulfuron-methyl | 50.0 | KHCO$_3$ | 7.0 | 54 | 3 |
| 9 | Thifensulfuron-methyl | 50.0 | KHCO$_3$ | 26.0 | 201 | 0 |
| 10 | Sulfometuron-methyl | 50.0 | None | — | 0 | 280, 310 |
| 11 | Sulfometuron-methyl | 50.0 | Na$_3$PO$_4$ | 2.9 | 13 | 280 |
| 12 | Sulfometuron-methyl | 50.0 | Na$_3$PO$_4$ | 5.6 | 25 | 270 |
| 13 | Sulfometuron-methyl | 50.0 | Na$_3$PO$_4$ | 11.4 | 50 | 290 |
| 14 | Sulfometuron-methyl | 50.0 | Na$_3$PO$_4$ | 22.4 | 99 | 50 |
| 15 | Sulfometuron-methyl | 36.5 | Na$_3$PO$_4$ | 32.8 | 197 | 1 |
| 16 | Sulfometuron-methyl | 50.0 | Na$_3$PO$_4$ | 45.0 | 198 | 2 |
| 17 | Bensulfuron-methyl | 50.0 | None | — | 0 | 330, 190 |
| 18 | Bensulfuron-methyl | 50.0 | Na$_2$CO$_3$ | 3.4 | 26 | 190 |
| 19 | Bensulfuron-methyl | 50.0 | Na$_2$CO$_3$ | 6.7 | 51 | 220 |
| 20 | Bensulfuron-methyl | 50.0 | Na$_2$CO$_3$ | 13.0 | 100 | 120 |
| 21 | Bensulfuron-methyl | 50.0 | Na$_2$CO$_3$ | 26.0 | 199 | 6 |
| 22 | Tribenuron-methyl | 50.0 | None | — | 0 | 70 |
| 23 | Tribenuron-methyl | 50.0 | Na$_2$CO$_3$ | 6.7 | 50 | 5 |
| 24 | Tribenuron-methyl | 50.0 | Na$_2$CO$_3$ | 26.5 | 198 | 0 |

Formulation Examples 1, 10, 17 and 22 illustrate conventional paste-extruded granular sulfonamide herbicide compositions containing little or no inorganic base. As can be seen from the data in Table 2, granular compositions prepared according to the process of this invention to contain about 50 equivalent percent of base resulted in much lower sulfonamide herbicide levels recovered in the acetonitrile wash solution when the sulfonamide herbicide was thifensulfuron-methyl; sodium carbonate was particularly efficacious on a % weight basis in the process of this invention to produce a thifensulfuron-methyl composition with low residue. For tribenuron-methyl 50 equivalent percent of base achieved a very substantial effect. For sulfometuron-methyl and bensulfuron-methyl, around 100 equivalent percent of base was needed to achieve a substantial effect, and increasing the amount of base to around 200 equivalent percent reduced the residue to negligible levels. This indicates that granular compositions prepared according to the process of this invention can result in significantly lower sulfonamide herbicide residues in spray equipment.

HERBICIDE TEST EXAMPLES

Formulation Preparation

Samples of formulations of Examples 1, 5 and 7 (thifensulfuron-methyl) and Examples 22 and 24 (tribenuron-methyl) were prepared according to the procedure described above in the Formulation Process Examples section.

Greenhouse Bioassay

The different formulations of thifensulfuron-methyl and tribenuron-methyl were evaluated in separate tests on *Convolvulus arvensis* L. (field bindweed) and *Galium aparine* L. (catchweed bedstraw). Both species were planted approximately 1 to 2 cm deep in 15-cm plastic pots. *Convolvulus arvensis* was thinned after emergence to two plants, and *Galium aparine* was thinned to three plants. Pots contained a synthetic growth medium (Redi-Earth® potting media, Scotts-Sierra Horticultural Products Company, Marysville, Ohio 43041) and were watered and fertilized for rapid growth. Metal halide lights providing 160 µE/m$^2$/s photosynthetically active radiation supplemented natural intensity during a 16-h photoperiod when light intensity was below 500 µE/m$^2$/s. Day temperature was 28±2° C. and night temperature was 22±2° C. *Convolvulus arvensis* and *Galium aparine* were each grown for 19 days and selected for uniformity before spraying. Plant heights of *Convolvulus arvensis* and *Galium aparine* were 10 to 13 cm and 4 to 6 cm, respectively.

Spray mixtures were made with deionized water at room temperature. Treatments were sprayed in a 94 L/ha volume approximately one hour after preparation. Treatments were replicated four times and were applied with a flat fan nozzle (TeeJet® flat-fan SS8001E model, Spraying Systems Co., Wheaton, Ill. 60188) at 51 cm height with spray pressure set at 138 kPa. The surfactant ceteareth-25 (polyethylene glycol ether of cetearyl alcohol (mixture of cetyl and stearyl alcohols) containing an average of 25 ethylene glycol units) was used at 0.1% of the spray volume where indicated. Plant shoots were weighed 15 days after treatment, and fresh weight inhibition was compared with untreated plants. The means, expressed as percent inhibition, are listed in Table 3.

TABLE 3

Comparison of the activity of thifensulfuron-methyl and tribenuron-methyl formulations on *Convolvulus arvensis* and *Galium aparine* with and without 0.1% w/w nonionic surfactant, ceteareth-25.

| Herbicide | Rate (g a.i./ha) | Formulation | Nonionic Surfactant | % Convolvulus Inhibition | % Galium Inhibition |
|---|---|---|---|---|---|
| Thifensulfuron-methyl | 15 | Ex. 1 | None | 35 | 87 |
| | | | Ceteareth-25 | 84 | 97 |
| | | Ex. 5 | None | 72 | 89 |
| | | | Ceteareth-25 | 91 | 98 |
| | | Ex. 7 | None | 69 | 88 |
| | | | Ceteareth-25 | 94 | 96 |
| | 45 | Ex. 1 | None | 61 | 94 |
| | | | Ceteareth-25 | 89 | 97 |
| | | Ex. 5 | None | 79 | 92 |
| | | | Ceteareth-25 | 94 | 99 |
| | | Ex. 7 | None | 78 | 96 |
| | | | Ceteareth-25 | 95 | 98 |
| Tribenuron-methyl | 15 | Ex. 22 | None | 81 | 61 |
| | | | Ceteareth-25 | 88 | 92 |
| | | Ex. 24 | None | 84 | 83 |
| | | | Ceteareth-25 | 90 | 94 |

TABLE 3-continued

Comparison of the activity of thifensulfuron-methyl and tribenuron-methyl formulations on *Convolvulus arvensis* and *Galium aparine* with and without 0.1% w/w nonionic surfactant, ceteareth-25.

| Herbicide | Rate (g a.i./ha) | Formulation | Nonionic Surfactant | % *Convolvulus* Inhibition | % *Galium* Inhibition |
|---|---|---|---|---|---|
| | 45 | Ex. 22 | None | 78 | 90 |
| | | | Ceteareth-25 | 92 | 96 |
| | | Ex. 24 | None | 89 | 91 |
| | | | Ceteareth-25 | 93 | 96 |

As can be seen from the results shown in Table 3, the paste-extruded thifensulfuron-methyl formulations prepared from mixtures containing base according to the process of this invention (i.e. Formulation Examples 5 and 7) provided much better control of *Convolvulus arvensis* than did the comparison formulation prepared from a mixture without added base (i.e. Formulation Example 1). While adding the surfactant ceteareth-25 to the spray solution enhanced the efficacy of comparison Formulation Example 1, the surfactant also further increased the efficacy of Formulation Examples 5 and 7, so that the best results in controlling *Convolvulus arvensis* were obtained from using ceteareth-25 with Formulation Examples 5 and 7 prepared according to the process of this invention. Also as can been seen from the results shown in Table 3, the paste-extruded tribenuron-methyl formulations prepared from mixtures containing base according the process of this invention (i.e. Formulation Example 24) provided much better control of *Convolvulus arvensis* at both application rates tested, and also much better control of *Galium aparine* at the lower (15 g a.i./ha) application rate than did the comparison formulation prepared from a mixture without added base (i.e. Formulation Example 22). The efficacy of both tribenuron-methyl formulations was increased by adding the surfactant ceteareth-25 to the spray solutions. In this bioassay experiment the formulations prepared according to the process of this invention showed the greatest advantage on weeds not well controlled by the comparison formulations at the application rates tested. These results demonstrate another remarkable benefit besides improved spray equipment clean-out properties for formulations prepared according to the process of the present invention.

What is claimed is:

1. A process for preparing a paste-extruded sulfonamide herbicide composition comprising
   (a) preparing a mixture comprising
      (i) from 2 to 90% by weight on a water-free basis of one or more active ingredients comprising at least one sulfonamide herbicide free acid;
      (ii) from 0 to 95% by weight on a water-free basis of one or more additives selected from the group consisting of wetting agents, dispersants, lubricants, anticaking agents, chemical stabilizers and diluents; and
      (iii) at least about 50 equivalent % of base selected from inorganic base equivalents having conjugate acid $pK_a$s at least 2.1 units greater than the highest $pK_a$ of the sulfonamide herbicide free acid component; the sum of the weight percents of all the ingredients in the mixture totaling 100% on a water-free basis; and
      (iv) sufficient water to make the mixture an extrudable paste;
   (b) extruding the mixture prepared in (a) through a die or screen to form extrudate; and
   (c) drying the extrudate.

2. The process of claim 1 wherein the mixture comprises at least about 75 equivalent % of base.

3. The process of claim 2 wherein the mixture comprises at least about 100 equivalent % of base.

4. The process of claim 1 wherein the base comprises an inorganic base selected from the group consisting of sodium hydrogen carbonate, sodium carbonate, sodium hydrogen phosphate, sodium phosphate, potassium hydrogen carbonate, potassium carbonate, potassium hydrogen phosphate and potassium phosphate.

5. The process of claim 4 wherein the base comprises an inorganic base selected from the group consisting of sodium carbonate, sodium phosphate, potassium carbonate and potassium phosphate.

6. The process of claim 5 wherein the base comprises sodium carbonate.

7. The process of claim 5 wherein the base comprises sodium phosphate.

8. The process of claim 7 wherein the sodium phosphate is in the faun of the dodecahydrate.

9. The process of claim 1 wherein the mixture comprises from about 0.5 to about 50% by weight of a saccharide on a water-free basis.

10. The process of claim 1 wherein at least one sulfonamide herbicide free acid is selected from the group consisting of amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flupyrsulfuron-methyl, flazasulfuron, foramsulfuron, halosulfuron-methyl, imazosulfuron, iodosulfuron-methyl, mesosulfuron-methyl, metsulfuron-methyl, nicosulfuron, oxasulfuron, primisulfuron-methyl, prosulfuron, pyrazosulfuron-ethyl, rimsulfuron, sulformeturon-methyl, sulfosulfuron, thifensulfuron-methyl, triasulfuron, tribenuron-inethyl, trifloxysulfuron, triflusulfuron-methyl, tritosulfuron, cloransulam-methyl, diclosulam, florasulam, flumetsulam, metosulam and penoxsulam.

11. The process of claim 10 wherein at least one sulfonamide herbicide free acid is selected from the group consisting of azimsulfuron, bensulfuron-methyl, chlorimuron-ethyl, chlorsulfuron, ethametsulfuron-methyl, flupyrsulfuron-methyl, metsulfuron-methyl, nicosulfuron, rimsulfuron, sulfometuron-methyl, thifensulfuron-methyl, tribenuron-methyl and triflusulfuron-methyl.

12. The process of claim 1 wherein at least one sulfonamide herbicide free acid is sulfometuron-methyl and the base comprises sodium phosphate.

13. The process of claim 1 wherein at least one sulfonamide herbicide free acid is thifensulfuron-methyl and the base comprises sodium carbonate.

14. The process of claim 1 wherein at least one sulfonamide herbicide free acid is tribenuron-methyl and the base comprises sodium carbonate.

15. The process of claim 1 wherein in (a) sufficient water to make an extrudable paste is added to a solid composition comprising from 2 to 90% by weight on a water-free basis of one or more active ingredients comprising at least one sulfonamide herbicide free acid, from 0.5 to 94% by weight on a water-free basis of a saccharide, from 1 to 20% by weight on a water-free basis of surfactant component, at least about 50 equivalent % of base selected from inorganic base equivalents having conjugate acid $pK_a$s at least 2.1 units greater than the highest $pK_a$ of the sulfonamide herbicide free acid component, and optionally other ingredients; the sum of the weight % of all the ingredients in the solid composition totaling 100% of a water-free basis; and at least 10% of the sulfonamide herbicide content in the solid composition being in free acid form.

16. The process of claim 1 further comprising a step of sifting the dried extrudate.

17. A process for preparing a paste-extruded sulfonamide herbicide composition comprising
   (a) preparing a mixture comprising
      (i) from 2 to 90% by weight on a water-free basis of one or more active ingredients comprising at least one sulfonamide herbicide free acid selected from the group consisting of amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flupyrsulfuron-methyl, flazasulfuron, foramsulfuron, halosulfuron-methyl, imazosulfuron, iodosulfuron-methyl, mesosulfuron-methyl, nicosulfuron, oxasul furon, primisulfuron-methyl prosulfuron, pyrazos ulfuron-ethyl, rimsulfuron, sulfometuron-methyl, sulfosulfuron, thifensulfuron-methyl, triasulfuron, tribenuron-methyl, trifloxysulfuron, triflusulfuron-methyl, trito sulfuron, cloransulam-methyl, diclosulam, florasulam, flumetsulam, metosulam and penoxsulam;
      (ii) from 0 to 95% by weight on a water-free basis of one or more additives selected from the group consisting of wetting agents, dispersants, lubricants, anticakitig agents, chemical stabilizers and diluents;
      (iii) at least about 50 equivalent % of base selected from inorganic base equivalents having conjugate acid $pK_a$s at least 2.1 units greater than the highest $pK_a$ of the sulfonamide herbicide free acid component;
      the sum of the weight percents of all the ingredients in the mixture totaling 100% on a water-free basis; and
      (iv) sufficient water to make the mixture an extrudable paste;
   (b) extruding the mixture prepared in (a) through a die or screen to form extrudate; and
   (c) drying the extrudate.

18. The process of claim 17 wherein the mixture comprises at least about 75 equivalent % of base.

19. The process of claim 18 wherein the mixture comprises at least about 100 equivalent % of base.

20. The process of claim 17 wherein the base comprises an inorganic base selected from the group consisting of sodium hydrogen carbonate, sodium carbonate, sodium hydrogen phosphate, sodium phosphate, potassium hydrogen carbonate, potassium carbonate, potassium hydrogen phosphate and potassium phosphate.

21. The process of claim 20 wherein the base comprises an inorganic base selected from the group consisting of sodium carbonate, sodium phosphate, potassium carbonate and potassium phosphate.

22. The process of claim 21 wherein the base comprises sodium carbonate.

23. The process of claim 21 wherein the base comprises sodium phosphate.

24. The process of claim 23 wherein the sodium phosphate is in the form of the dodecahydrate.

25. The process of claim 17 wherein the mixture comprises from about 0.5 to about 50% by weight of a saccharide on a water-free basis.

26. The process of claim 17 wherein in (a) sufficient water to make an extrudable paste is added to a solid composition comprising from 2 to 90% by weight on a water-free basis of one or more active ingredients comprising at least one sulfonamide herbicide free acid, from 0.5 to 94% by weight on a water-free basis of a saccharide, from 1 to 20% by weight on a water-free basis of surfactant component, at least about 50 equivalent % of base selected from inorganic base equivalents having conjugate acid $pK_a$s at least 2.1 units greater than the highest $pK_a$ of the sulfonamide herbicide free acid component, and optionally other ingredients; the sum of the weight % of all the ingredients in the solid composition totaling 100% of a water-free basis; and at least 10% of the sulfonamide herbicide content in the solid composition being in free acid form.

27. The process of claim 17 further comprising a step of sifting the dried extrudate.

28. A process for preparing a paste-extruded sulfonamide herbicide composition comprising
   (a) preparing a mixture comprising
      (i) from 2 to 90% by weight on a water-free basis of one or more active ingredients comprising at least one sulfonamide herbicide free acid;
      (ii) from 0 to 95% by weight on a water-free basis of one or more additives selected from the group consisting of wetting agents, dispersants, lubricants, anticaking agents, chemical stabilizers and diluents;
      (iii) at least about 50 equivalent % of base selected from an inorganic base equivalent selected from the group consisting of sodium hydrogen carbonate, sodium hydrogen phosphate, sodium phosphate, potassium hydrogen carbonate, potassium carbonate, potassium hydrogen phosphate, potassium phosphate, sodium pyrophosphate, sodium tripolyphosphate, sodium trisilicate, sodium trimetaphosphate, sodium hexametaphosphate, sodium polyphosphate, ammonium hydrogen phosphate, lithium oxide, lithium hydroxide, lithium carbonate, sodium hydroxide, lithium phosphate, lithium metasilicate, lithium orthosilicate, potassium hydroxide, sodium metasilicate, sodium orthosilicate and potassium pyrophosphate;
      having conjugate acid $pK_a$s at least 2.1 units greater than the highest $pK_a$ of the sulfonamide herbicide free acid component;
      the sum of the weight percents of all the ingredients in the mixture totaling 100% on a water-free basis; and
      (iv) sufficient water to make the mixture an extrudable paste;
   (b) extruding the mixture prepared in (a) through a die or screen to form extrudate; and
   (c) drying the extrudate.

29. The process of claim 1 wherein the mixture further comprises from about 0.5 to about 50% by weight of a disaccharide on a water-free basis.

30. The process of claim 29 wherein at least one sulfonamide herbicide free acid is sulfometuron-methyl and the base comprises sodium phosphate.

31. The process of claim 29 wherein at least one sulfonamide herbicide free acid is thifensulfuron-methyl and the base comprises sodium carbonate.

32. The process of claim 29 wherein at least one sulfonamide herbicide free acid is tribenuron-methyl and the base comprises sodium carbonate.

33. The process of claim 1 wherein the mixture comprises two or more active ingredients.

34. A process for preparing a paste-extruded sulfonamide herbicide composition comprising
   (a) preparing a mixture comprising
      (i) from 2 to 90% by weight on a water-free basis of one or more active ingredients comprising at least one sulfonamide herbicide free acid, (ii) from 0 to 95% by weight on a water-free basis of one or more additives selected from the group consisting of wetting agents, dispersants, lubricants, anticaking agents, chemical stabilizers and diluents, (iii) at least about 50 equivalent % of base selected from inorganic base equivalents having conjugate acid $pK_a$s at least 2.1 units greater than the highest $pK_a$ of the sulfonamide herbicide free acid component; the sum of the weight percents of all the ingredients in the mixture totaling 100% on a water-free basis and the base component comprising a hydrated form of sodium phosphate, and (iv) sufficient water to make the mixture an extrudable paste;

(b) extruding the mixture prepared in (a) through a die or screen to form extrudate; and (c) drying the extrudate.

35. The process of claim 34, wherein the hydrated form of sodium phosphate is the dodecahydrate.

36. The process of claim 1 wherein at least one sulfonamide herbicide free acid is rimsulfuron.

37. The process of claim 1 wherein at least one sulfonamide herbicide free acid is sulfometuron-methyl.

38. The process of claim 1 wherein at least one sulfonamide herbicide free acid is thifensulfuron-methyl.

39. The process of claim 1 wherein at least one sulfonamide herbicide free acid is tribenuron-methyl.

* * * * *